(12) United States Patent
Valenta et al.

(10) Patent No.: US 7,482,010 B2
(45) Date of Patent: *Jan. 27, 2009

(54) NON-ANAPHYLACTIC FORMS OF GRASS POLLEN PHL P 6 ALLERGEN AND THEIR USE

(75) Inventors: Rudolf Valenta, Theresienfeld (AT); Susanne Vrtala, Vienna (AT); Sabine Stummfoll, St. Peter (AT); Hans Grönlund, Lidingö (SE); Monika Grote, Münster (DE); Luca Vangelista, Padua (IT); Annalisa Pastore, London (GB); Wolfgang R. Sperr, Vienna (AT); Peter Valent, Vienna (AT); Dietrich Kraft, Vienna (AT)

(73) Assignee: Phadia AB, Uppsala (SE)

( * ) Notice: Subject to any disclaimer, the term of this patent is extended or adjusted under 35 U.S.C. 154(b) by 417 days.

This patent is subject to a terminal disclaimer.

(21) Appl. No.: 10/305,238

(22) Filed: Nov. 27, 2002

(65) Prior Publication Data
US 2003/0143239 A1 Jul. 31, 2003

Related U.S. Application Data

(62) Division of application No. 09/696,169, filed on Oct. 26, 2000, now Pat. No. 6,572,859.

(60) Provisional application No. 60/164,148, filed on Nov. 8, 1999.

(30) Foreign Application Priority Data
Oct. 29, 1999 (SE) ..................... 9903950

(51) Int. Cl.
*A61K 39/00* (2006.01)
(52) U.S. Cl. ............... 424/185.1; 424/184.1; 424/193.1; 424/805; 424/810; 435/7.1; 435/7.92; 530/326; 530/806; 530/868
(58) Field of Classification Search ........................ None
See application file for complete search history.

(56) References Cited

U.S. PATENT DOCUMENTS

| 5,026,545 | A |   | 6/1991 | Saint-Remy et al. |
| 5,091,171 | A | * | 2/1992 | Yu et al. ............ 424/642 |

FOREIGN PATENT DOCUMENTS

| WO | WO9843657 | 10/1998 |
| WO | WO9916467 | 4/1999 |
| WO | 9934826 | 7/1999 |
| WO | WO9934826 | 7/1999 |

OTHER PUBLICATIONS

Chapman, M. pp. 51-64 of Allergens and Allergen Immunotherapy, 3rd edition, 2004, Marcel Dekker Inc.*
Matthews et al., Clin. Sci. (Lond.), 1984, 67:541-549.*
Vrtala et al., J. Clin. Invest. 1997, 99:1673-1681.*
Petersen et al., J. Allergy Clin. Immunol. 1995, vol. 95, No. 1, part 2, pp. 306.*
Download from wordnet.princeton.edu, Feb. 2, 2007, 1 page.*
Petersen et al., Int Arch Allergy Immunol. Sep. 1995;108(1)55-59.*
Blumenthal et al., in Allergens and Allergen Immunotherapy, 3rd edition, 2004, Marcel Dekker, Inc., pp. 37-50.*
Petersen et al., *Int. Arch. Allergy. Immunol.*, vol. 108 (1995) pp. 55-59.
G. Schramm et al., *J. Immunol.*, vol. 162, No. 4 (1999) pp. 2406-2414.
S. Vrtala et al., *J. Immunol.*, vol. 163 (1999) pp. 5489-5496.
P. Norman, *Advances in Medicine*, vol. 41 (1996) pp. 681-713.
S. Vrtala et al., *J. Clin. Invest.*, vol. 99, No. 7 (1997) pp. 1673-1681.
S. Schenk et al., *J. Allergy Clin. Immunol.*, vol. 96, No. 6 (1995) pp. 986-996.
R.J. Joost van Neervan et al., *J. Immunol.*, vol. 151, No. 4 (1993) pp. 2326-2335.
C. Ebner et al., *J. Immunol.*, vol. 150, No. 3 (1993) pp. 1047-1054.
P. S. Norman, *Cur. Opinion in Immunol.*, vol. 5 (1993) pp. 968-973.
T. J. Briner et al., *Proc. Natl. Acad. Sci.*, vol. 90 (1993) pp. 7608-7612.
C. Nicodemus et al., *Int. Arch. Allergy Immunol.*, vol. 113 (1997) pp. 326-328.
A. Litwin et al., *Clinical and Experimental Allergy*, vol. 21 (1991) pp. 457-465.
U. Muller et al., *J. Allergy Clin. Immunol.*, vol. 101, No. 6, part 1 (Jun. 1998) pp. 747-754).
A. Petersen et al., *Int. Arch Allergy Immunol.*, vol. 108 (1995) pp. 49-54.
P. Norman et al., *Int Arch Allergy Immunol.*, vol. 113 (1997) pp. 224-226.
Mohapatra S, et al, "In pursuit of the 'holy grail: recombinant allergens and peptides as catalysts for the allergen-specific immunotherapy", *Allergy*, 1995:50 (suppl 25): 37-44.
Lockey et al, "Allergens and Allergen Immunotherapy", *Marcel Dekker, Inc.*, 647-649. 2004.

* cited by examiner

*Primary Examiner*—Michael Szperka
(74) *Attorney, Agent, or Firm*—Porter, Wright, Morris & Arthur LLP

(57) ABSTRACT

The invention relates to a hypoallergenic immunogenic molecule derived from the Phl p 6 allergen, wherein the Phl p 6 molecule has an N-terminal and/or C-terminal deletion which makes the molecule at least substantially lack IgE binding capacity. The invention also relates to a hypoallergenic immunogenic combination of molecules derived from the Phl p 6 allergen, comprising (i) a Phl p 6 molecule having an N-terminal deletion which makes the molecule at least substantially lack IgE binding capacity, and (ii) a Phl p 6 molecule having a C-terminal deletion which makes the molecule at least substantially lack IgE binding capacity, which two molecules together encompass the complete sequence of Phl p 6. The invention further relates to the use of the hypoallergenic immunogenic molecule or molecule mixture in hyposensitization and diagnosis.

13 Claims, 11 Drawing Sheets

SEQUENCE LISTING

```
<160> NUMBER OF SEQ ID NOS: 22

<210> SEQ ID NO 1
<211> LENGTH: 29
<212> TYPE: DNA
<213> ORGANISM: Artificial Sequence
<220> FEATURE:
<223> OTHER INFORMATION: Primer derived from Phleum pratense

<400> SEQUENCE: 1
gggaattcca tatggggaag gccacgacc                                   29

<210> SEQ ID NO 2
<211> LENGTH: 45
<212> TYPE: DNA
<213> ORGANISM: Artificial Sequence
<220> FEATURE:
<223> OTHER INFORMATION: Primer derived from Phleum pratense

<400> SEQUENCE: 2
cggggtaccc tagtggtggt ggtggtggtg gggcgccttt gaaac                 45
```

<210> SEQ ID NO 3
<211> LENGTH: 29
<212> TYPE: DNA
<213> ORGANISM: Artificial Sequence
<220> FEATURE:
<223> OTHER INFORMATION: Primer derived from Phleum pratense

<400> SEQUENCE: 3
gggaattcca tatggcagac aagtataag                              29

<210> SEQ ID NO 4
<211> LENGTH: 45
<212> TYPE: DNA
<213> ORGANISM: Artificial Sequence
<220> FEATURE:
<223> OTHER INFORMATION: Primer derived from Phleum pratense

<400> SEQUENCE: 4
ccggaattcc tagtggtggt ggtggtggtg cgcgccgggc ttgac            45

<210> SEQ ID NO 5
<211> LENGTH: 4
<212> TYPE: PRT
<213> ORGANISM: Phleum pratense

<400> SEQUENCE: 5

Gly Lys Ala Thr
1

<210> SEQ ID NO 6
<211> LENGTH: 4
<212> TYPE: PRT
<213> ORGANISM: Phleum pratense

<400> SEQUENCE: 6

Lys Ala Thr Thr
1

<210> SEQ ID NO 7
<211> LENGTH: 4
<212> TYPE: PRT
<213> ORGANISM: Phleum pratense

<400> SEQUENCE: 7

Lys Tyr Lys Thr
1

<210> SEQ ID NO 8
<211> LENGTH: 138
<212> TYPE: PRT
<213> ORGANISM: Phleum pratense

<400> SEQUENCE: 8

Met Ala Ala His Lys Phe Met Val Ala Met Phe Leu Ala Val Ala Val
1               5                   10                  15

Val Leu Gly Leu Ala Thr Ser Pro Thr Ala Glu Gly Gly Lys Ala Thr
            20                  25                  30

Thr Glu Glu Gln Lys Leu Ile Glu Asp Val Asn Ala Ser Phe Arg Ala
        35                  40                  45

Ala Met Ala Thr Thr Ala Asn Val Pro Pro Ala Asp Lys Tyr Lys Thr
    50                  55                  60

Phe Glu Ala Ala Phe Thr Val Ser Ser Lys Arg Asn Leu Ala Asp Ala
65                  70                  75                  80

```
Val Ser Lys Ala Pro Gln Leu Val Pro Lys Leu Asp Glu Val Tyr Asn
                85                  90                  95

Ala Ala Tyr Asn Ala Ala Asp His Ala Ala Pro Glu Asp Lys Tyr Glu
            100                 105                 110

Ala Phe Val Leu His Phe Ser Glu Ala Leu Arg Ile Ile Ala Gly Thr
        115                 120                 125

Pro Glu Val His Ala Val Lys Pro Gly Ala
    130                 135
```

```
<210> SEQ ID NO 9
<211> LENGTH: 750
<212> TYPE: DNA
<213> ORGANISM: Phleum pratense

<400> SEQUENCE: 9
ctatccctcc tacaaaccaa cgcacgagta gcaatggcag cgcacaagtt catggtggcg     60
atgttcctcg ctgttgccgt tgtgttgggc ttggccacat ccccaactgc agagggaggg    120
aaggccacga ccgaggagca aaaattgatc gaggacatca atgccagctt tagggcggcc    180
atggccacca ctgctaacgt ccctccagca gacaagtata agacattcga agccgccttc    240
acggtgtcct caaagagaaa cctcgctgac gccgtttcaa aggcgcccca gctggtcccc    300
aagctcgatg aagtctacaa cgccgcctac aatgctgccg atcatgccgc ccagaagac     360
aagtatgaag ccttcgtcct tcactttttc gaggctctcc acatcatcgc cggtaccccc    420
gaggtccacg ctgtcaagcc cggcgcgtag ttgttcagca cggtcaagat ccttgacagc    480
gtcgctgcca ccggcgctgc agccaacact gccagtggct aaaaaattcg actagctcct    540
tcatacaatg aatacacatg tatcattcaa acatactact gtacagtatg tgcatgacct    600
agcggcgagc atttttttta tgattaatct tttatacatg ggcgtgatcg agcgtgtgca    660
tatgtgtaat aattaatttt ttattttgat ttgaaattgt aatcctgata agaaatgcga    720
ttaagtccat ttatgaaaaa aaaaaaaaaa                                     750

<210> SEQ ID NO 10
<211> LENGTH: 571
<212> TYPE: DNA
<213> ORGANISM: Phleum pratense

<400> SEQUENCE: 10
ccaacgcacg agtagcaatg gcagcgcaca agttcatggt ggcgatgttc ctcgctgttg     60
ccgttgtgtt gggcttggcc acatccccaa ctgcagaggg agggaaggcc acgaccgagg    120
agcaaaaatt gattgaggac gtcaatgcca gctttagggc ggccatggcc accactgcta    180
acgtccctcc agcagacaag tataagacat tcgaagccgc cttcacggtg tcctcaaaga    240
gaaacctcgc tgacgccgtt tcaaaggcgc ccagctggt ccccaagctc gatgaagtct    300
acaacgccgc ctacaatgct gccgatcatg ccgcccaga agacaagtat gaagccttcg    360
tccttcactt ttccgaggct ctccgtatca tcgccggtac cccgaggtt cacgctgtca    420
agcccggcgc gtagttgttc agcacggtca agatccttga cagcgtcgct gccaccggcg    480
ctgcagccaa cactgccagt ggctaaaaaa ttcgactagc tccttcatac aatgaataca    540
catgtatcat tcaaaaaaaa aaaaaaaaaa a                                   571

<210> SEQ ID NO 11
<211> LENGTH: 647
<212> TYPE: DNA
<213> ORGANISM: Phleum pratense
```

<400> SEQUENCE: 11

```
accgaggagc aaaaattgat cgaggacgtc aatgccagct ttagggcggc catggccacc        60
actgctaacg tccctccagc agacaagtat aagacattag aagccgcctt cacggtgtcc       120
tcaaagagaa acctcgctga cgccgtctca aaggcgcccc agctcgtccc caagctcgat       180
gaagtctaca acgccgccta caatgctgcc gatcatgccg ccccagaaga caagtatgaa       240
gccttcgtcc ttcactttc cgaggctctc cgtatcatcg ccggtacccc cgaggtccac        300
gctgtcaagc ccgcgcgta gttgttcagc acggtcaaga tccttgacag cgtcgctgcc       360
accggtgctg cagccaacac tgccagtggc taaaaagttc gaccagctct tcatacaat       420
gaatacacat gtatctttca aacatactac tgtacagtat gtgcatgacc tagcggcgag       480
cattttttt atgattaatc ttttatacat gggcgtgatc gagcgtgtgc atatgtgtaa        540
taattaattt cttatttga tttgaaattg taatcctgat aagaaatgcg attaagtcca        600
tttatgaaat atagatggtc cgtcgttatt taaaaaaaaa aaaaaaa                     647
```

<210> SEQ ID NO 12
<211> LENGTH: 572
<212> TYPE: DNA
<213> ORGANISM: Phleum pratense

<400> SEQUENCE: 12

```
gcagacaagt ataagacatt cgaagccgcc ttcacggtgt cctcaaagag aaacctcgct        60
gacgccgttt caaaggcgcc ccagctggtc cccaagctcg atgaagtcta caacgccgcc       120
tacaatgctg ccgatcatgc cgccccagaa gacaagtatg aagccttcgt ccttcacttt       180
tccgaggctc tccacatcat cgccggtacc cccgaggtcc acgctgtcaa gcccggcgcg       240
tagttgttca gcacggtcaa gatccttgac agcgtcgctg ccaccggcgc tgcagccaac       300
actgccagtg gctaaaaaat tcgactagct ccttcataca atgaatacac atgtatcatt       360
caaacatact actgtacagt atgtgcatga cctagcggcg agcatttttt ttatgattaa       420
tcttttatac atgggcgtga tcgagcgtgt gcatatgtgt aataattaat tttttatttt       480
gatttgaaat tgtaatcctg ataagaaatg cgattaagtc catttaaaaa aaaaaaaaa       540
aaaaaaaaa aaaaaaaaa aaaaaaaaa aa                                        572
```

<210> SEQ ID NO 13
<211> LENGTH: 474
<212> TYPE: DNA
<213> ORGANISM: Phleum pratense

<400> SEQUENCE: 13

```
tcaaaggcgc cccagctggt ccccaagctc gatgaagtct acaacgccgc ctacaatgct        60
gccgatcatg ccgccccaga agacaagtat gaagccttcg tccttcactt ttccgaggct       120
ctccacatca tcgccggtac cccgaggtc cacgctgtca agcccggcgc gtagttgttc        180
agcacggtca gatccttga cagcgtcgct gccaccggcg ctgcagccaa cactgccagt       240
ggctaaaaaa ttcgactagc tccttcatac aatgaataca catgtatcat tcaaacatac       300
tactgtacag tatgtgcatg acctagcggc gagcattttt tttatgatta atctttata       360
catgggcgtg atcgagcgtg tgcatatgtg taataattaa ttttttattt tgatttgaaa       420
ttgtaatcct gataagaaat gcgattaagt ccatttatga aaaaaaaaa aaaa             474
```

<210> SEQ ID NO 14

-continued

```
<211> LENGTH: 554
<212> TYPE: DNA
<213> ORGANISM: Phleum pratense

<400> SEQUENCE: 14
cagctggtcc ccaagctcga tgaagtctac aacgccgcct acaatgctgc cgatcatgcc      60
gccccagaag acaagtatga agccttcgtc cttcactttt ccgaggctct ccacatcatc     120
gccggtaccc ccgaggtcca cgctgtcaag cccggcgcgt agttgttcag cacggtcaag     180
atccttgaca cgtcgctgc accggcgct gcagccaaca ctgccagtgg ctaaaaaatt       240
cgactagctc cttcatacaa tgaatacaca tgtatcattc aaacatacta ctgtacagta     300
tgtgcatgac ctagcggcga gcatttttt tatgattaat cttttataca tgggcgtgat      360
cgagcgtgtg catatgtgta ataattaatt ttttattttg atttgaaatt gtaatcctga     420
taagaaatgc gattaagtcc atttatgaaa tatagatggt ctgtcgttat ttaaaaaaaa     480
aaaaaaaaaa aaaaaaaaaa aaaaaaaaaa aaaaaaaaaa aaaaaaaaaa aaaaaaaaaa     540
aaaaaaaaaa aaaa                                                       554

<210> SEQ ID NO 15
<211> LENGTH: 138
<212> TYPE: PRT
<213> ORGANISM: Phleum pratense

<400> SEQUENCE: 15

Met Ala Ala His Lys Phe Met Val Ala Met Phe Leu Ala Val Ala Val
1               5                   10                  15

Val Leu Gly Leu Ala Thr Ser Pro Thr Ala Glu Gly Gly Lys Ala Thr
            20                  25                  30

Thr Glu Glu Gln Lys Leu Ile Glu Asp Ile Asn Ala Ser Phe Arg Ala
        35                  40                  45

Ala Met Ala Thr Thr Ala Asn Val Pro Pro Ala Asp Lys Tyr Lys Thr
    50                  55                  60

Phe Glu Ala Ala Phe Thr Val Ser Ser Lys Arg Asn Leu Ala Asp Ala
65                  70                  75                  80

Val Ser Lys Ala Pro Gln Leu Val Pro Lys Leu Asp Glu Val Tyr Asn
                85                  90                  95

Ala Ala Tyr Asn Ala Ala Asp His Ala Ala Pro Glu Asp Lys Tyr Glu
            100                 105                 110

Ala Phe Val Leu His Phe Ser Glu Ala Leu His Ile Ile Ala Gly Thr
        115                 120                 125

Pro Glu Val His Ala Val Lys Pro Gly Ala
    130                 135

<210> SEQ ID NO 16
<211> LENGTH: 138
<212> TYPE: PRT
<213> ORGANISM: Phleum pratense

<400> SEQUENCE: 16

Met Ala Ala His Lys Phe Met Val Ala Met Phe Leu Ala Val Ala Val
1               5                   10                  15

Val Leu Gly Leu Ala Thr Ser Pro Thr Ala Glu Gly Gly Lys Ala Thr
            20                  25                  30

Thr Glu Glu Gln Lys Leu Ile Glu Asp Val Asn Ala Ser Phe Arg Ala
        35                  40                  45

Ala Met Ala Thr Thr Ala Asn Val Pro Pro Ala Asp Lys Tyr Lys Thr
```

```
                50                  55                  60
Phe Glu Ala Ala Phe Thr Val Ser Ser Lys Arg Asn Leu Ala Asp Ala
 65                  70                  75                  80

Val Ser Lys Ala Pro Gln Leu Val Pro Lys Leu Asp Glu Val Tyr Asn
                 85                  90                  95

Ala Ala Tyr Asn Ala Ala Asp His Ala Ala Pro Glu Asp Lys Tyr Glu
                100                 105                 110

Ala Phe Val Leu His Phe Ser Glu Ala Leu Arg Ile Ile Ala Gly Thr
            115                 120                 125

Pro Glu Val His Ala Val Lys Pro Gly Ala
        130                 135
```

<210> SEQ ID NO 17
<211> LENGTH: 106
<212> TYPE: PRT
<213> ORGANISM: Phleum pratense

<400> SEQUENCE: 17

```
Thr Glu Glu Gln Lys Leu Ile Glu Asp Val Asn Ala Ser Phe Arg Ala
 1               5                  10                  15

Ala Met Ala Thr Thr Ala Asn Val Pro Pro Ala Asp Lys Tyr Lys Thr
                20                  25                  30

Leu Glu Ala Ala Phe Thr Val Ser Ser Lys Arg Asn Leu Ala Asp Ala
            35                  40                  45

Val Ser Lys Ala Pro Gln Leu Val Pro Lys Leu Asp Glu Val Tyr Asn
         50                  55                  60

Ala Ala Tyr Asn Ala Ala Asp His Ala Ala Pro Glu Asp Lys Tyr Glu
 65                  70                  75                  80

Ala Phe Val Leu His Phe Ser Glu Ala Leu Arg Ile Ile Ala Gly Thr
                 85                  90                  95

Pro Glu Val His Ala Val Lys Pro Gly Ala
                100                 105
```

<210> SEQ ID NO 18
<211> LENGTH: 80
<212> TYPE: PRT
<213> ORGANISM: Phleum pratense

<400> SEQUENCE: 18

```
Ala Asp Lys Tyr Lys Thr Phe Glu Ala Ala Phe Thr Val Ser Ser Lys
 1               5                  10                  15

Arg Asn Leu Ala Asp Ala Val Ser Lys Ala Pro Gln Leu Val Pro Lys
                20                  25                  30

Leu Asp Glu Val Tyr Asn Ala Ala Tyr Asn Ala Ala Asp His Ala Ala
            35                  40                  45

Pro Glu Asp Lys Tyr Glu Ala Phe Val Leu His Phe Ser Glu Ala Leu
         50                  55                  60

His Ile Ile Ala Gly Thr Pro Glu Val His Ala Val Lys Pro Gly Ala
 65                  70                  75                  80
```

<210> SEQ ID NO 19
<211> LENGTH: 57
<212> TYPE: PRT
<213> ORGANISM: Phleum pratense

<400> SEQUENCE: 19

```
Ser Lys Ala Pro Gln Leu Val Pro Lys Leu Asp Glu Val Tyr Asn Ala
 1               5                  10                  15
```

```
Ala Tyr Asn Ala Ala Asp His Ala Ala Pro Glu Asp Lys Tyr Glu Ala
            20                  25                  30

Phe Val Leu His Phe Ser Glu Ala Leu His Ile Ile Ala Gly Thr Pro
        35                  40                  45

Glu Val His Ala Val Lys Pro Gly Ala
    50                  55

<210> SEQ ID NO 20
<211> LENGTH: 53
<212> TYPE: PRT
<213> ORGANISM: Phleum pratense

<400> SEQUENCE: 20

Gln Leu Val Pro Lys Leu Asp Glu Val Tyr Asn Ala Ala Tyr Asn Ala
1               5                   10                  15

Ala Asp His Ala Ala Pro Glu Asp Lys Tyr Glu Ala Phe Val Leu His
            20                  25                  30

Phe Ser Glu Ala Leu His Ile Ile Ala Gly Thr Pro Glu Val His Ala
        35                  40                  45

Val Lys Pro Gly Ala
    50

<210> SEQ ID NO 21
<211> LENGTH: 57
<212> TYPE: PRT
<213> ORGANISM: Phleum pratense

<400> SEQUENCE: 21

Met Ala Ala His Lys Phe Met Val Ala Met Phe Leu Ala Val Ala Val
1               5                   10                  15

Val Leu Gly Leu Ala Thr Ser Pro Thr Ala Glu Gly Gly Lys Ala Thr
            20                  25                  30

Thr Glu Glu Gln Lys Leu Ile Glu Asp Val Asn Ala Ser Phe Arg Ala
        35                  40                  45

Ala Met Ala Thr Thr Ala Asn Val Pro
    50                  55

<210> SEQ ID NO 22
<211> LENGTH: 57
<212> TYPE: PRT
<213> ORGANISM: Phleum pratense

<400> SEQUENCE: 22

Gly Lys Ala Thr Thr Glu Glu Gln Lys Leu Ile Glu Asp Ile Asn Ala
1               5                   10                  15

Ser Phe Arg Ala Ala Met Ala Thr Thr Ala Asn Val Pro Pro Ala Asp
            20                  25                  30

Lys Tyr Lys Thr Phe Glu Ala Ala Phe Thr Val Ser Ser Lys Arg Asn
        35                  40                  45

Leu Ala Asp Ala Val Ser Lys Ala Pro
    50                  55
```

NON-ANAPHYLACTIC FORMS OF GRASS POLLEN PHL P 6 ALLERGEN AND THEIR USE

This application is a divisional application of application Ser. No. 09/696,169, filed on Oct. 26, 2000, now U.S. Pat. No. 6,572,859, the entire contents of which are hereby incorporated by reference and for which priority is claimed under 35 U.S.C. § 120; and this application claims priority of Application Nos. 9903950-S filed in Sweden on Oct. 29, 1999 and U.S. Provisional Application No. 60/164,148 filed in the USA on Nov. 8, 1999 under 35 U.S.C. § 119(e).

FIELD OF THE INVENTION

The present invention relates to non-anaphylactic, i.e. hypoallergenic, forms of the major timothy grass pollen allergen Phl p 6 and the use of the forms for hyposensitization and for diagnosis. The invention also relates to a method for hyposensitization of a mammalian individual, typically a human individual, suffering from type I allergy against the Phl p 6 allergen.

BACKGROUND OF THE INVENTION

Type I allergy is a genetically determined hypersensitivity disease that affects more than 20% of the population in industrialized countries (1). As a consequence of this immunodisorder, allergic patients produce IgE antibodies against per se innocuous, mostly air-born proteins from pollen, mites, moulds and animal hair/dander. The symptoms of Type I allergy (allergic rhinitis, conjunctivitis, allergic asthma and anaphylactic shock) result from allergen-induced crosslinking of effector cell (mast cell, basophil)-bound IgE antibodies and subsequent release of inflammatory mediators (2). Since approximately 40% of allergic individuals suffer symptoms following contact with grass pollen, research has concentrated on the characterization of relevant grass pollen allergens by protein and immunochemical methods (3). While groups of major allergens have been identified as cross-reactive moieties that occur in most grass species (4), nothing was known concerning their nature and biological functions.

The recent application of molecular biological techniques to allergen characterization has revealed the primary structures of allergens and facilitated the production of recombinant allergens for diagnostic and therapeutic purposes (5). Components of the plant cytoskeleton (e.g., profilin) (6) as well as calcium-binding pollen proteins (7) have been identified as relevant allergens. The fact that allergic patients exhibit immediate type reactions upon contact with various unrelated allergen sources thus can be explained by cross-reactivity of their IgE antibodies with ubiquitous allergens. Evidence that group 1 grass pollen allergens belong to a family of cell wall-loosening proteins (expansins) (8) and grass group 5 allergens may possess RNAse activity (9) has restimulated ideas that the biological function of a given protein may be related to its allergenicity. The recent findings that major grass pollen allergens can either become attached to small sized particles (e.g., group 1 allergens to diesel exhaust (10)) or may become airborn as small pollen subcompartments (e.g., group 5 allergens in amyloplasts (11)) would provide a possible mechanism of how certain allergens may be able to reach the deep airways of patients and to elicit allergic asthma.

Therapy of Type I allergic diseases is currently performed by pharmacological treatment and by specific immunotherapy. Specific immunotherapy has been established already early in this century (Noon, Lancet 1 (1911) 1572-1573) and involves the systemic application of increasing doses of allergens for extended periods.

Although specific immunotherapy is recognized as effective treatment, the occurrence of anaphylactic side effects represents one of the major disadvantages of this therapy. To reduce anaphylactic reactions the use of T-cell epitopes has recently been proposed for allergen specific immunotherapy (Briner et al., Proc. Natl. Acad. Sci. USA 90 (1993) 7608-7612, and Norman, Curr. Opin. Immunol. 5 (1993) 986-973). Allergens harbour a great variety of different T-cell epitopes (Ebner et al., J. Immunol 150 (1993) 1047-1054; Joost-van-Neerven et al., J. Immunol. 151 (1993) 2326-2335; and Schenket al., J. Allergy Clin. Immunol. 96 (1995) 986-996) which may overlap with continuous IgE-epitopes. To prevent crosslinking of effector cell (mast cell, basophil) bound IgE and mediator release, T-cell epitopes and IgE epitopes need to be dissected.

Vrtala et al., J. Clin. Invest. 99(7) 1673-1681 (1997) and WO 99/16467 disclose a novel strategy of reducing the anaphylactic activity of the major birch allergen Bet v 1 by disrupting the three dimensional structure by expressing two parts of the Bet v 1 cDNA representing amino acids 1-74 and 75-160 in *Escherichia coli*. In contrast to the complete recombinant Bet v 1, the recombinant fragments showed almost no allergenicity. Both non-anaphylactic fragments induced proliferation of human Bet v 1-specific T cell clones, indicating that they harboured all dominant T cell epitopes and therefore could be used for safe and specific T cell immunotherapy. The success of this strategy was believed to be due to the fact that the Bet v 1 allergen possesses discontinuous (i.e. conformational) IgE epitopes rather than continuous IgE epitopes as is the case for many other allergens.

In contrast to the major birch allergen Bet v 1, the major timothy grass pollen allergen Phl p 6 contains continuous (sequential) IgE epitopes and would therefore not be susceptible to the above fragmentation strategy to reduce anaphylactic activity as outlined above.

SUMMARY OF THE INVENTION

According to the present invention, however, it has surprisingly and most unexpectedly been found that Phl p 6 deletion variants may be constructed by genetic (recombinant) or synthetic fragmentation, which fragments may be used for specific immunotherapy of grass pollen allergy with reduced anaphylactic side effects. Such fragments with strongly reduced anaphylactic ability will below be referred to as non-anaphylactic or hypoallergenic.

DETAILED DESCRIPTION

In a first aspect of the present invention there is provided a hypoallergenic immunogenic molecule derived from the Phl p 6 allergen, wherein the Phl p 6 molecule has an N-terminal and/or C-terminal deletion which makes the molecule at least substantially lack IgE binding capacity.

The N-terminal or C-terminal deletion may be a terminal truncation of the allergen. The deletion may also be internal within the N-terminal or C-terminal part of the allergen, respectively.

The allergen molecule fragments may be produced by recombinant DNA techniques or peptide synthetic chemistry as is per se well known to the skilled person.

In a second aspect, the present invention provides a hypoallergenic immunogenic combination of molecules derived from the Phl p 6 allergen, comprising (i) a Phl p 6 molecule having an N-terminal deletion which makes the molecule at least substantially lack IgE binding capacity, and (ii) a Phl p 6 molecule having a C-terminal deletion which makes the molecule at least substantially lack IgE binding capacity, which two molecules together encompass the complete amino acid sequence of the Phl p 6 allergen.

For together encompassing the complete amino acid sequence of Phl p 6, the respective sequences of the two Phl p 6 molecules may overlap or be contiguous.

The sizes of the N-terminal and C-terminal deletions of the Phl p 6 allergen necessary for the fragments to be useful for the purposes of the invention, i.e. that the fragments are (i) immunogenic and (ii) non-IgE reactive, may readily be determined by the skilled person. Thus, the lack or presence of IgE binding ability of a particular N-terminal or C-terminally deletion molecule may easily be determined, the lack of IgE reactivity indicating that the molecule may be applied without or with low risk of inducing anaphylactic side effects. Immunogenic activity of the molecules may be determined by their capability of being recognized by a polyclonal antiserum to the complete Phl p 6 allergen. In this way fragments and fragment combinations, respectively, may be selected which have a very high likelyhood of being capable of eliciting immune responses which protect against the complete allergen.

A third aspect of the invention is a specific hyposensitization therapy. Such therapy may be performed as known in the art for protein allergens and encompasses administering repeatedly to the mammal, typically a human individual, suffering from type I allergy against the allergen an immunogen that is capable of raising an IgG immune response against the allergen. The immunogen may be admixed with suitable adjuvants such as aluminium oxide. Administration may be done systemically, for instance by injection, infusion, etc, but also the oral route has been suggested in order to expose the intestinal part of the immune system. See also Norman PS, "Current status of immunotherapy for allergies and anaphylactic reactions" Adv. Internal. Medicine 41 (1996) 681-713.

Here, the immunogen to be administered may be an immunogenic molecule according to the first aspect of the invention, or a mixture of such molecules, preferably, the above-mentioned hypoallergenic immunogenic combination of molecules derived from the Phl p 6 allergen according to the second aspect of the invention, i.e. (i) a Phl p 6 molecule having an N-terminal deletion which makes the molecule at least substantially lack IgE binding capacity, and (ii) a Phl p 6 molecule having a C-terminal deletion which makes the molecule at least substantially lack IgE binding capacity, which two molecules together encompass the complete amino acid sequence of Phl p 6.

More specifically, the immunogens may be used to induce antibody responses in a patient, and/or to elicit T cell response, and/or to modulate antibody and T cell repsonse to induce tolerance.

A fourth aspect of the present invention provides the use the immunogen according to the first aspect, or the combination of immunogens according to the second aspect, as an antigen in an immunoassay for detecting specific antibodies of the IgA, IgD, IgE, IgG or IgM class directed against the Phl p 6 allergen from which the immunogen(s) derive. Appropriate assay variants involve formation of a ternary immune complex between the immunogen, sample antibody and an antibody directed against the Ig-class of interest. The sample may be any Ig-containing biological fluids, for instance a blood derived sample (serum, plasma, whole blood), CSF, etc. Especially, the hypoallergenic fragments may be used for diagnostic monitoring (e.g. IgG measurements, measurement of T cell responses) during therapy when inducing a new immune response against the fragments.

Sequence Listing

SEQ ID NO: 1—Artificial Primer (nucleotide sequence—29 residues);

SEQ ID NO: 2—Artificial Primer (nucleotide sequence—45 residues);

SEQ ID NO: 3—Artificial Primer (nucleotide sequence—29 residues);

SEQ ID NO: 4—Artificial Primer (nucleotide sequence—45 residues);

SEQ ID NO: 5—*Phelum pratense* (peptide sequence—4 amino acids);

SEQ ID NO: 6—*Phelum pratense* (peptide sequence—4 amino acids);

SEQ ID NO: 7—*Phelum pratense* (peptide sequence—4 amino acids);

SEQ ID NO: 8—full length recombinant Phl p 6 (peptide sequence—138 amino acids);

SEQ ID NO: 9—full length c142 (nucleotide sequence—750 residues);

SEQ ID NO: 10—full length c223 (nucleotide sequence—571 residues);

SEQ ID NO: 11—full length c171 (nucleotide sequence—647 residues);

SEQ ID NO: 12—full length c121 (nucleotide sequence—572 residues);

SEQ ID NO: 13—full length c233 (nucleotide sequence—474 residues);

SEQ ID NO: 14—full length c146 (nucleotide sequence—554 residues);

SEQ ID NO: 15—c142 (peptide sequence—138 amino acids);

SEQ ID NO: 16—c223 (peptide sequence—138 amino acids);

SEQ ID NO: 17—c171 (peptide sequence—106 amino acids);

SEQ ID NO: 18—c121 (peptide sequence—80 amino acids);

SEQ ID NO: 19—c233 (peptide sequence—57 amino acids);

SEQ ID NO: 20—c146 (peptide sequence—53 amino acids);

SEQ ID NO: 21—peptide sequence of a 28 amino acid leader peptide and recombinant Phl p 6 (amino acids 1-29); and SEQ ID NO: 22 —peptide sequence of recombinant Phl p 6 (amino acids 1-57).

The invention will now be illustrated by the following non-limiting Example.

EXAMPLE

Materials and Methods

Biological Materials, Patients Sera, Antisera, Recombinant Allergens.

Pollen from timothy grass (*Phelum pratense*), rye grass (*Lolium perenne*), rye (*Secale cereale*), Kentucky blue grass (*Poa pratensis*), wheat (*Triticum sativum*), cultivated oat (*Avena sativa*) and common reed (*Phragmites communis*) were from Allergon AB, (Välinge, Sweden). Timothy grass seeds were purchased from Austrosaat, (Vienna, Austria) and grown for 4 weeks to obtain fresh leaves and roots. Patients allergic to grass pollen were characterized as described (4). The rabbit anti-celery profilin antiserum (RP1) is described (12). A rabbit anti-rPhl p 6 antiserum was raised against purified, recombinant Phl p 6 using Freunds adjuvans (Charles River, Kissleg, Germany). Recombinant timothy grass pollen allergens, rPhl p 1, rPhl p 2 and rPhl p 5 were purified as described (13). Recombinant timothy grass pollen profilin was purified by poly (L-proline) affinity chromatography (6).

Isolation and Characterization of cDNAs Coding for Phl p 6 Isoforms/Fragments.

Threehundred and fifty IgE-reactive clones were isolated from an expression cDNA library constructed from mature timothy grass pollen in phage λgt 11 (14). Six cDNAs (c121, c142, c146, c171, c223, c233) with sequence homology to a Phl p 6-encoding cDNA (15) were subcloned into plasmid pUC18 and sequenced (16, 17). Sequences were analyzed using the McVector program (Kodak, Rochester, N.Y.). Search for Phl p 6-homologous protein sequences was done with the FastA program (GCG package) (18) in the SwissProt database. The sequences of Hol l 5 and Hor v 5 allergens were retrieved from the EMBL database. Multiple sequence alignment was produced with ClustalW (19) and edited by hand. The GDE sequence editor (S. Smith, Harvard University, Cambridge, Mass.) and COLORMASK (J. Thompson, EMBL, Heidelberg, Germany) were used to colour conserved residues with related properties (19). Protein secondary structure and surface accessibility predictions were done with the PHD program on the EMBL PredictProtein server (20).

Mapping of Phl p 6 IgE Epitopes, Expression and Purification of Recombinant Phl p 6.

The IgE binding capacity of phage clones expressing Phl p 6 isoforms and fragments was investigated by a plaque lift assay (21). The DNA coding for the mature Phl p 6 allergen was PCR-amplified from the clone 142 DNA, subcloned into the NdeI/Eco R I site of pET-17b. Recombinant Phl p 6 was expressed in *E. coli* BL 21 (DE 3) in liquid culture. Cells were suspended in 25 mM Imidazole, pH 7.4, 0.1% Triton X-100 and lysed by addition of lysozyme (20 µg/g cells) for 30 minutes at room temperature as well as by freeze-thawing cycles. DNA was digested with DNAse I (0.1 mg/g cell pellet) for 20 minutes at room temperature. The protein extract was centrifuged for 20 min at 10.000×g (Sorvall RC5C; SS34 rotor) to remove insoluble materials. rPhl p 6 was enriched in a precipitate obtained by addition of ammonium sulfate (40-60% w/v). The precipitate was dissolved in 10 mM Tris pH 6, dialyzed against this buffer and after centrifugation (20 min, 10,000 g, Sorvall RC5C; SS34 rotor) was applied to a diethylaminoethyl cellulose-Sepharose column (Pharmacia). Unbound proteins were eluted with 10 mM Tris, pH 6, 4% v/v isopropanol. Fractions containing more than 80% pure Phl p 6 were adjusted to pH 8 with NaOH and subjected to a second chromatography step on a diethylaminoethyl cellulose-Sepharose column. Elution of bound proteins with a 0-0.5 M NaCl gradient at pH 8 yielded fractions containing pure rPhl p 6 which were dialyzed against $H_2O_{dd}$.

MALDI-TOF (Matrix Assisted Laser Desorption and Ionisation-Time of Flight) and CD (Circular Dichroism) Analysis of Purified Recombinant Phl p 6.

Laser desorption mass spectra were acquired in a linear mode with a time-of-flight Compact MALDI II instrument (Kratos, Manchester, UK) (piCHEM, Graz, Austria). CD spectra were recorded on a Jasco J-710 spectropolarimeter fitted with a Jasco PTC-348WI peltier type temperature control system and interfaced with a Fisons HAAKE GH water bath. Far ultraviolet CD spectra were recorded at 20° C. in a 2 mm path-length quartz cuvette (Hellma, Mullheim, Baden, Germany) at a protein concentration of 7 µM. Thermal denaturation of Phl p 6 was monitored by recording the ellipticity during temperature increase (50° C./h) at 220 nm. The reversibility of the unfolding process was checked by measuring the restoration of the CD signal upon cooling (50° C./h) to the starting temperature (20° C.). The fraction of folded protein was calculated as $F=1-U$, where $U=(\Theta 220-\Theta N)/(\Theta U-\Theta N)$. $\Theta N$ is the ellipticity of the protein in the native state and $\Theta U$ that of the denatured protein. For rPhl p 6, $\Theta U$ was assumed to be equal to $\Theta 220$ at 85° C. and $\Theta N$ to $\Theta 220$ at 20° C.

IgE-Binding Capacity of Recombinant Phl p 6, Cross-Reactivity with Natural Phl p 6 and Other Timothy Grass Pollen Allergens.

The prevalence of IgE anti-rPhl p 6 reactivity was determined in sera from 171 grass pollen allergic patients and, for control purposes, in sera from non-atopic persons by ELISA (13). The presence of cross-reactive IgE epitopes on natural and rPhl p 6 was investigated by IgE immunoblot inhibition experiments (4). A possible immunological relationship between rPhl p 6 and recombinant timothy grass pollen allergens (rPhl p 1, rPhl p 2, rPhl p 5) (13) was studied by ELISA competition as described (4).

Histamine Release Experiments.

Granulocytes were isolated from heparinized blood samples of grass pollen allergic individuals containing rPhl p 6-reactive IgE antibodies by dextran sedimentation (22). Cells were incubated with increasing concentrations of purified rPhl p 5, rPhl p 6, and with an anti-human IgE antibody (E124.2.8 Dε2, Immunotech, Marseille, France). Histamine released into the supernatants was measured by radioimmunoassay (Immunotech, Marseille, France).

Skin Testing.

After informed consent was obtained skin prick tests were performed on the forearms of the individuals as described (23). Individuals were pricked with 20 µl aliquots containing different concentrations (1 µg/ml, 10 µg/ml, 100 µg/ml) of purified rPhl p 6, rPhl p 5 and with timothy grass pollen extract, histamine and sodium chloride (ALK, Horsholm, Denmark).

Analysis of the Presence of Phl p 6-Related Allergens in Other Grass Species and Tissue-Specific Expression of Phl p 6.

Protein extracts from pollens, leaves and roots were obtained by homogenizing the tissues in SDS-sample buffer (24). Insoluble materials were removed by centrifuging the extracts (10.000×g, 20 min; Sorvall RC5C, SS34 rotor). Protein extracts were separated by 14% SDS-PAGE (25) and blotted onto nitrocellulose (26). Nitrocellulose strips were probed with a rabbit anti-celery profilin antiserum, RP1, (12), the rabbit anti-rPhl p 6 antiserum and the latter rabbits preimmune serum. Bound rabbit antibodies were detected with a 1:1000 diluted $^{125}$I-labeled donkey anti-rabbit Ig antiserum (Amersham).

In situ Localization of Phl p 6 by Immunogold Electron Microscopy.

Timothy grass pollen grains were unhydrously fixed as described (27). Ultrathin sections were incubated with equal concentrations of either rabbit anti-rPhl p 6 Ig (Ig: protein G-purified immunoglobulin fraction) or preimmune Ig. Bound rabbit antibodies were detected with goat anti-rabbit IgG antibodies coupled to 10 nm colloidal gold particles (Plano, Wetzlar, Germany) (27).

Construction of hypoallergenic Phl p (*Phelum pratense*) deletion variants.

N-terminal and C-terminal Phl p 6 deletion variants were generated to represent aa 1-57 and aa 31-110. cDNAs coding for Phl p 6 aa 1-57 and Phl p 6 aa 31-110 were obtained by PCR amplification of the Phl p 6 cDNA (clone #142) using the following oligonucleotide primers:

Expression of Phl p 6 Deletion Variants in *E. coli* and Testing of their IgE-Binding Capacity Recombinant Phl p 6 aa 1-57 and Phl p 6 aa 31-110 were expressed in *E. coli* Bl 21 (DE 3) by induction with 0.5 mM isopropyl-β-thiogalactopyranoside at an $OD_{600}$ of 0.8 in liquid culture for 5 h at 37° C. Equal amounts of rPhl p 6, rPhl p 6 aa 1-57 and rPhl p 6 aa 31-110 were separated by SDS-PAGE and blotted onto nitrocellulose.

Nitrocellulose strips were incubated with serum IgE from allergic individuals, nonallergic control persons, with a rabbit anti-Phl p 6 antiserum and a rabbit preimmunserum. Bound IgE antibodies were detected with $^{125}$I-labelled anti-human IgE antibodies and bound rabbit antibodies with $^{125}$I-labelled donkey anti-rabbit antibodies.

RESULTS

Isolation and characterization off cDNAs coding for isoforms/fragments of Phl p 6.

Six cDNA clones (c142, c223, c171, c121, c233, c146), coding for Phl p 6 isoforms/fragments were isolated from a timothy grass pollen λgt11 library with serum IgE from a grass pollen allergic patient. The sequences of the described clones have been deposited in the GenBank database (Accession numbers: Y16955-Y16960). The deduced amino acid sequences of Phl p 6 (clone 142) contained a 28 aa hydrophobic leader peptide. A molecular mass of 11.8 kDa and a pI of 5.5 were calculated for the mature Phl p 6 (clone 142) protein which starts with a glycine residue and shows a high content of alanine residues (20.9%). The computer-aided secondary structure analysis on Phl p 6 indicates a predominant helical content and the calculation of solvent accessibility predicts that many of the N-terminal amino acids are solvent (exposed while most of the C-terminal amino acids appeared buried. A search for sequence motifs revealed the presence of one potential N-linked glycosylation site (NAS: aa 15-17), one N-terminal myristoylation site (GKAT(SEQ ID NO: 5): aa

```
For Phl p 6 aa 1-57:
5': GGG AAT TCC ATA TGG GGA AGG CCA CGA CC 3'
(SEQ ID NO:1)
5': CGG GGT ACC CTA GTG GTG GTG GTG GTG GTG GGG CGC CTT TGA AAC 3'
(SEQ ID NO:2)

For Phl p 6 aa 31-110:
5': GGG AAT TCC ATA TGG CAG ACA AGT ATA AG 3'
(SEQ ID NO:3)
5': CCG GAA TTC CTA GTG GTG GTG GTG GTG GTG CGC GCC GGG CTT GAC 3'
(SEQ ID NO:4)
```

Eco R I and Kpn I site are printed in italics, Nde I sites and a His-tag, which has been introduced at the C-terminus, are underlined.

The PCR-products were cut with Nde I/Kpn I (aa 1-57) or with Nde I/Eco R I (aa 31-110), purified by preparative agarose gel electrophoresis, subcloned into plasmid pET-17b (Novagen) and transformed into *E. coli* BL 21(DE3) (Novagen). Colonies expressing the correct deletion variants were identified by immunoscreening using a rabbit anti-Phl p 6 antiserum. DNA from positive clones was isolated using Qiagen tips (Qiagen, Hilden, Germany) and sequenced (MWG-Biotech, Hilden, Germany).

1-4), two cAMP-dependent protein kinase phosphorylation sites (KATT(SEQ ID NO: 6): aa 2-5; KYKT(SEQ ID NO: 7): aa 33-36) and two peroxisomal targeting sequences (GKA: aa 1-3; SKA: aa 54-56). The deduced Phl p 6 amino acid sequence displayed identity with a recently submitted Phl p 6 sequence (15) and similarities with the N-terminal portions of group 5 grass pollen allergens. However, Phl p 6 specific IgE shows little or no crossreactivity with group 5 allergens. A comparison with group 5 grass pollen allergens is given in Vrtala, S., et al., J. Immunol. 1999, 163(10): 5489-5496 (37) (the disclosure of which is incorporated by reference herein). FIG. 1A therein shows a multiple sequence alignment, secondary structure and solvent accessibility prediction of Phl p 6 variants and group 5 allergens.

The Phl p 6 N-terminus is Relevant for IgE Binding.

Nitrocellulose-bound β-gal-fused complete (c223, c142), N-terminally truncated rPhl p 6 (c171, c121, c233, c146) and, for control purposes, β-gal alone were exposed to serum IgE from 9 grass pollen allergic individuals and a non-allergic person (FIG. 1). Results obtained showed that the two complete Phl p 6 isoforms and a Phl p 6 fragment lacking only 4 of the N-terminal amino acids strongly bound IgE from all grass pollen allergic patients tested and that the IgE binding capacity of the partial Phl p 6 clones decreased depending on the number of amino acids which were absent from the proteins' N-terminus. A partial clone (clone 121) lacking the N-terminal 30 amino acids had almost completely lost its IgE binding capacity (FIG. 1).

E. coli Expression and Purification of Recombinant Phl p 6. IgE Binding Capacity of Purified rPhl p 6.

rPhl p 6 was overexpressed in E. coli BL21 (DE3). A combination of several purification steps yielded pure and soluble rPhl p 6 (approximately 5 mg protein/liter E. coli culture) which by SDS-PAGE was identified as one of the low molecular weight timothy grass pollen allergens (FIG. 2A). MALDI-TOF analysis of purified recombinant Phl p 6 resulted in two mass/charge peaks of 11790 and 5896 corresponding to the MH+ and M2H2+ species of the sample which were in agreement with the deduced Phl p 6 molecular mass (11789 Da).

In 128 sera from 171 grass pollen allergic patients but in no serum from 10 non-allergic individuals rPhl p 6-specific IgE antibodies were detected. Preabsorption of sera from grass pollen allergic patients with rPhl p 6 led to a great reduction of IgE binding to a 10-14 kDa moiety in nitrocellulose-blotted timothy grass pollen extract indicating that rPhl p 6 and natural Phl p 6 share IgE epitopes. ELISA competition experiments demonstrated that only a small percentage (<20%) of Phl p 5-specific IgE could be preabsorbed with rPhl p 6. IgE binding to rPhl p 1, rPhl p 2 and recombinant timothy grass profilin was not reduced after preincubation of sera with rPhl p 6. These results identify Phl p 6 as a major allergen which is distinct from other grass pollen allergens.

rPhl p 6 Folds in a Stable all Alpha Helical Conformation.

The far-ultraviolet CD spectrum of purified rPhl p 6 (FIG. 2B) indicates that the protein contains a considerable amount of alpha-helical secondary structure. The spectrum is characterized by two broad minima at 208 nm and 220 nm and a maximum at 191 nm. The secondary structure prediction (37) is in good agreement with the CD measurements as it indicates predominant alpha helical secondary structure content. The unfolding transition of rPhl p 6 is monophasic and highly cooperative with a melting point of 61° C. At 85° C., rPhl p 6 assumes a random coil conformation, with a typical minimum at 200 nm. rPhl p 6 shows a high degree of folding reversibility, evident from the cooling curve profile (FIG. 2C) and the far-UV spectrum recorded at 20° C. after cooling from 85° C. (FIG. 2B).

Recombinant Phl p 6 Induces Dose Dependent Basophil Histamine Release and Immediate Type Skin Reactions in Grass Pollen Allergic Patients.

Purified rPhl p 6 induced specific and dose-dependent histamine release from basophils of a grass pollen allergic patient (FIG. 3A). rPhl p 5 which represents a highly active grass pollen allergen (14, Valenta and Flicker, unpublished data) induced maximal release already at a lower concentration compared to rPhl p 6. In four grass pollen allergic patients but not in the non-allergic individuals, rPhl p 6, rPhl p 5 and timothy grass pollen extract induced immediate type skin reactions (Table 1; FIG. 3B). While no reactions to sodium chloride were observed, histamine induced wheal reactions in all individuals tested (Table 1; FIG. 3B).

Group 6 Allergens Represent Pollen-Specific Proteins.

While major groups of grass pollen allergens occur in pollens of most grass species (4), group 6 allergens were reported to occur exclusively in timothy grass (*Phelum pratense*) pollen (15). A rabbit anti-rPhl p 6 antiserum cross-reacted with group 5 allergens in nitrocellulose blotted pollen extracts from various monocots (*Phelum pratense, Lolium perenne, Secale cereale, Triticum sativum, Avena sativa, Phragmites communis*) between 25-28 kDa (FIG. 4A, lanes 2). Phl p 6 or Phl p 6-related allergens at 11 kDa were detected exclusively in pollens from *Phelum pratense* and *Poa pratensis*. Although a putative N-glycosylation site was found in the aminoacid sequence deduced from the Phl p 6 cDNA sequence, comparable molecular weights observed for natural and recombinant Phl p 6 exclude heavy glycosylation of natural Phl p 6 (FIGS. 4A, 2A). Rabbit anti-rPhl p 6 antibodies strongly reacted with Phl p 6 at 11 kDa in nitrocellulose-blotted timothy grass pollen but not with leaf or root extracts (FIG. 4B, lanes 2). Profilin was detected in all three tissues at approximately 14 kDa (FIG. 4B, lanes 1).

Immunelectronmicroscopical Localization of Phl p 6 in Timothy Grass Pollen.

Using post-embedding immunogold electron microscopy, rabbit anti-rPhl p 6 antibodies bound to the numerous polysaccharide (P–) particles which fill much of the interior of a mature timothy grass pollen grain (FIG. 4C). The greatest accumulation of gold particles was observed on sectioned surfaces of the P-particles indicating that Phl p 6 is present on rather than in the P-particles. Little (cytosol, exine) or no (mitochondria, intine) anti-rPhl p 6 immunoreactivity was observed in other parts of the pollen grain. Likewise almost no gold particles were detected in the amyloplasts. This localization pattern, taken together with our finding that a rabbit anti-rPhl p 5 antiserum failed to label the P-particles (data not shown) excludes the possibility that the immunolabeling of the P-particles resulted from the presence of cross-reactive group 5 allergens. Control experiments performed with pre-immune Ig yielded only a few non-specifically adsorbed gold particles (FIG. 4D).

Phl p 6 Deletion Variants (aa 1-57, aa 31-110) exhibit strongly reduced IgE binding capacity.

Nitrocellulose-blotted complete rPhl p 6 (FIG. 5A), rPhl p 6 variant aa 1-57 (FIG. 5B) and rPhl p 6 variant aa 31-110 (FIG. 5C) were exposed to 13 sera from grass pollen allergic patients, to a serum from a non-atopic person and to a rabbit anti-rPhl p 6 antiserum. While all 13 grass pollen allergic patients displayed IgE reactivity to complete recombinant Phl p 6 (FIG. 5A), variant aa 1-57 was recognized by serum 11 and weakly by serum 13 (FIG. 5B). Phl p 6 variant aa 31-110 reacted only weakly with serum 7 and 11 (FIG. 5C). Serum from the non-atopic individual failed to react with complete rPhl p 6 and the deletion variants. The rabbit anti-rPhl p 6 antiserum showed reactivity of comparable intensity to complete rPhl p 6 and the two deletion variants (FIGS. 5A-C: lanes 15) whereas the rabbits preimmune serum showed no reactivity in the molecular weight range of the molecules (FIGS. 5A-C: lanes 16).

IgG1-Reactivity of Mouse anti-rPhl p 6 or anti-rPhl p 6 aa 31-110 antisera to rPhl p 6

Mouse IgG 1 raised against complete rPhl p 6 and rPhl p 6 aa 31-110 react with rPhl p 6 (Table II).

rPhl p 6 Derivatives have a Greatly Reduced Capacity to Induce Histamine Release Granulocytes from a patient allergic to grass pollen were incubated with various concentrations of purified rPhl p 6, rPhl p 6 aa 1-57, rPhl p 6 aa 31-110, rPhl p 6 aa 1-33 or an anti-IgE mAb (E124.2.8 De2, Immunotech, Marseilles, France). Histamine released into the supernatant was measured by RIA (Immunotech)(FIG. 6). Purified rPhl p 6 induced a specific and dose-dependent histamine release from basophils of a patient allergic to grass pollen, whereas rPhl p 6-derivatives aa 1-57 and aa 31-110 did not induce any histamine release up to a concentration of 1 µg/ml. Phl p 6 aa 1-33 induced a 50% release of histamine at a concentration of 1 µg/ml, which represents an approximately 1000 fold reduction of histamine release compared to complete rPhl p 6.

DISCUSSION

Approximately 40% of allergic patients display immediate type symptoms after contact with grass pollen (3). We have isolated cDNAs coding for isoforms and fragments of a major timothy grass pollen allergen, designated Phl p 6. Phl p 6 represents a 11.8 kDa protein allergen which is recognized by IgE antibodies of 75% of grass pollen allergic patients. The prevalence of IgE recognition of rPhl p 6 is thus in accordance with that reported earlier for natural Phl p 6 and indicates that carbohydrate moieties do not play a relevant role in IgE recognition of Phl p 6 (28, 29). In agreement with peptide sequence data obtained for natural Phl p 6 we found that the deduced amino acid sequence of rPhl p 6 shows a high degree of sequence homology with the N-terminal portions of group 5 grass pollen allergens, a family of 25-35 kDa major grass pollen allergens (29, 14). Due to the presence of an N-terminal hydrophobic leader peptide, Phl p 6 represents an independent allergen, rather than a group 5 allergen fragment. In agreement with the proposal of other authors who analyzed a Phl p 6 encoding cDNA clone (15) we suggest that group 5 and group 6 allergens may have evolved from common ancestor genes similar as has been described for group 1 and group 2/3 grass pollen allergens (30). The assumption that Phl p 6 belongs to an independent group of grass pollen allergens is also supported by our finding that Phl p 6 shares few cross-reactive IgE epitopes with group 5 and no with other grass pollen allergens. The prediction of solvent accessibility indicated that many of the Phl p 6 N-terminal amino acids are solvent exposed while most of the C-terminal amino acid residues appeared to be buried. While no proof, this finding is in agreement with data obtained from the IgE epitope mapping experiments which indicate that the proteins N-terminus is critically involved in IgE recognition. It is however equally possible that the N-terminus itself represents a dominant IgE epitope or that deletion of the N-terminus affects conformational Phl p 6 IgE epitopes.

Expression of Phl p 6 in *E. coli* yielded large amounts of soluble and folded recombinant protein which contained almost exclusive alpha helical secondary structure. The alpha helical fold of Phl p 6 is a further confirmation that there are no common structural features which predispose a certain protein to behave as an allergen. While Phl p 6 is very likely an all alpha helical protein, Bet v 1, the major birch pollen allergen (31) and Bet v 2, birch profilin (32) have a mixed alpha beta fold. As revealed by CD spectroscopical analysis, rPhl p 6 shares with other immunologically unrelated pollen allergens (e.g., Bet v 1 (33), Bet v 2 (6, 32)) the remarkable intrinsic tendency to refold into a stable conformation after denaturation. Another feature that is shared by Phl p 6 and other important plant allergens is its high expression in pollen tissue. The fact that most of the plant allergens characterized so far are predominantly expressed in mature pollen may therefore be interpreted as a footprint of sensitization via the respiratory tract (34).

By immunogold electron microscopy, Phl p 6 was primarily localized on the P-particles of mature pollen. P-particles are small polysaccharide-containing bodies which represent up to 30% of the contents of the dormant pollen grain and, during pollen germination transfer material into the growing pollen-tube wall (35, 36). The occurence of Phl p 6 on the P-particles may be of clinical relevance as P-particles could act as small-sized (<2.5 micron) and therefore respirable allergen-carriers that bring Phl p 6 in immediate contact with the bronchial mucosa. A P-particle-linked intrusion of Phl p 6 into the deeper respiratory tract would thus explain the high prevalence (75%) of sensitization against this allergen although only a few grass species (*Phelum pratense, Poa pratensis*) contained rabbit anti-rPhl p 6-reactive moieties in the low (10-12 kDa) molecular weight range.

The *Escherichia coli*-expressed purified recombinant Phl p 6 allergen reacted with IgE antibodies of the majority of grass pollen allergic patients and induced basophil histamine release as well as immediate type skin reactions. It may therefore be used for in vitro as well as in vivo (skin test) diagnosis of grass pollen allergy. Our finding that deletion of the N-terminal portion of Phl p 6 dramatically reduced the allergens IgE binding capacity gave rise to the idea that it may be possible to construct Phl p 6 deletion variants which may be used for specific immunotherapy of grass pollen allergy with reduced anaphylactic side effects. A similar strategy was recently applied to disrupt the conformational IgE epitopes of the major birch pollen allergen Bet v 1 (23) but could not be predicted for Phl p 6 because the latter molecule contained continuous IgE epitopes. We produced N-terminally and C-terminally truncated versions of Phl p 6, of which the variant aa 1-57 and aa 31-110 showed almost completely abolished IgE binding capacity. We propose to use these two hypoallergenic Phl p 6 variants produced as recombinant molecules or by peptide chemistry as candidate vaccines against grass pollen allergy.

TABLES AND FIGURES

TABLE 1. Immediate type skin reactivity to rPhl p 6. Four grass pollen allergic patients (HP, SF, CS, LW) and two non-allergic individuals (SV, SS) were skin tested with purified rPhl p 6, rPhl p 5, with natural timothy grass pollen extract, histamine and isotonic sodium chloride. Results are displayed as the mean diameters (mm) of the wheal reaction.

TABLE II. IgG-1-reactivity of mouse anti-rPhl p 6 or anti-rPhl p 6 aa 31-110 antisera to rPhl p 6.

REFERENCES

Figure 1:
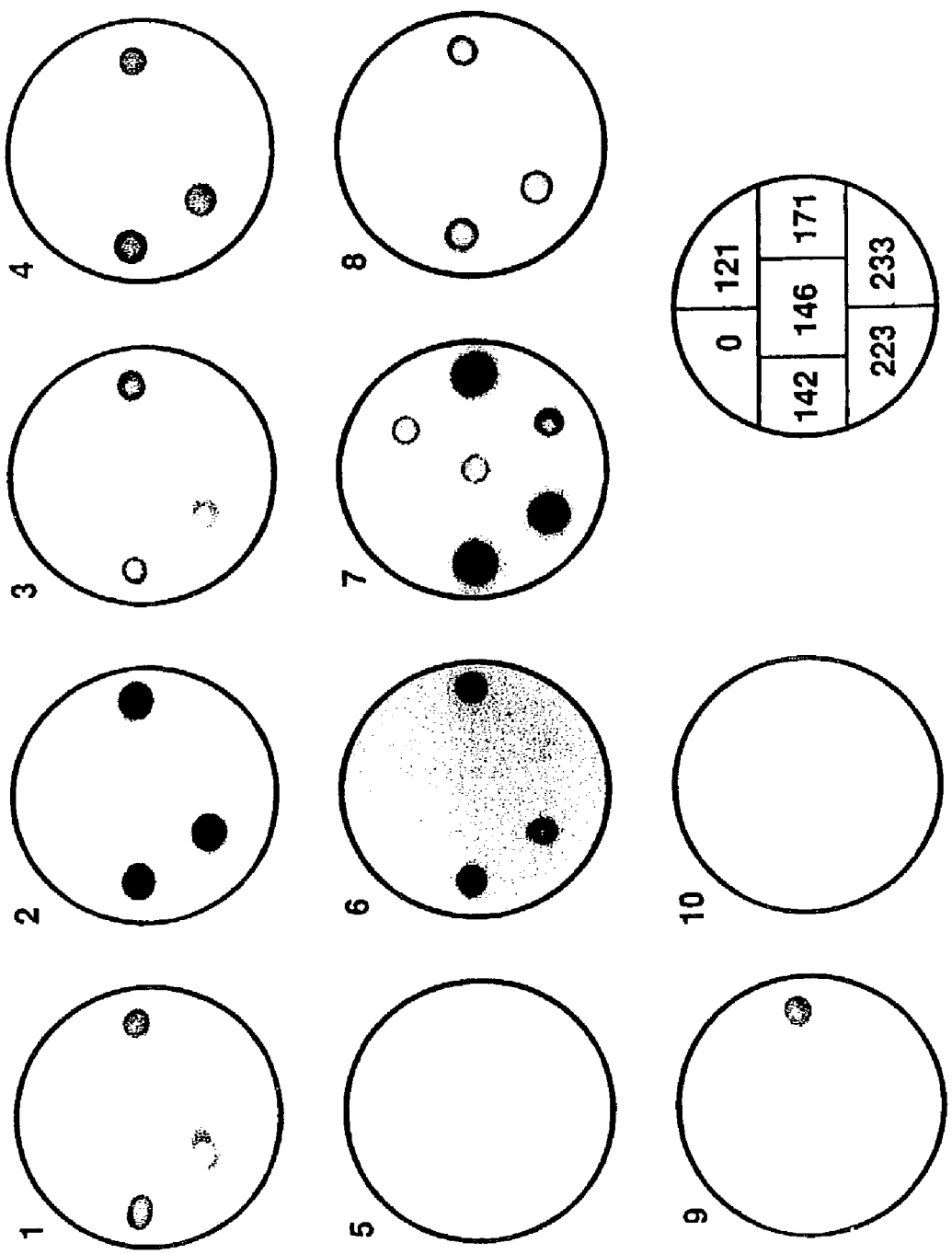
FIG. 1. IgE reactivity of rPhl p 6 isoforms and fragments. Nitrocellulose filters containing proteins from recombinant λgt 11 phage expressing two Phl p 6 isoforms (c142, c223), Phl p 6 fragments (c121, c146, c171, c233) and for control purposes, λgt11 wild type phage (0) were probed with serum IgE from 9 grass pollen-allergic patients (1-9) and from one non-allergic individual (10).
Figure 2A:
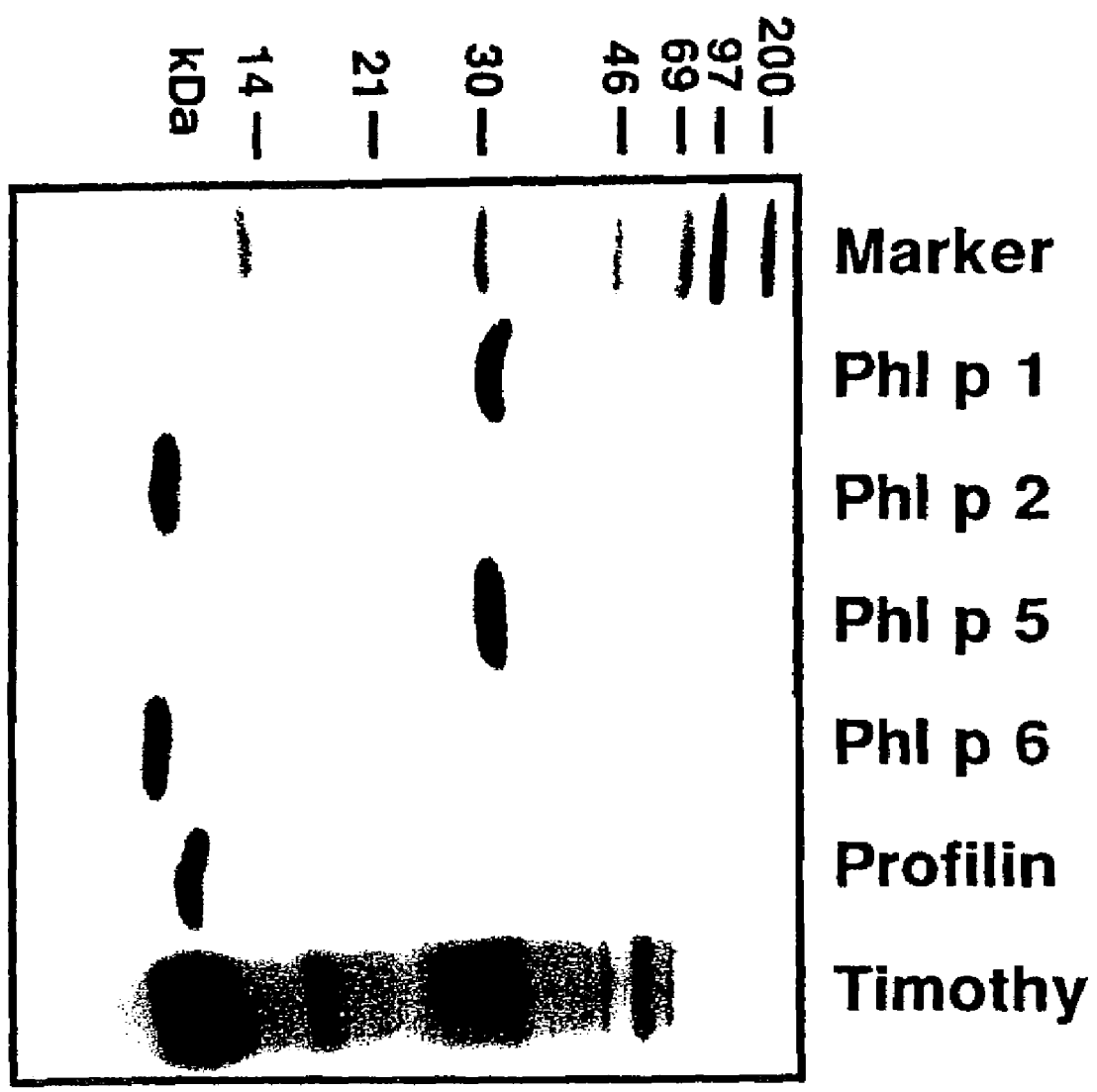
FIG. 2. A, Purity of recombinant timothy grass pollen allergens. Coomassie brilliant blue-stained SDS-PAGE containing purified, recombinant timothy grass pollen allergens (Phl p 1, Phl p 2, Phl p 5, Phl p 6, timothy grass pollen profilin) and natural timothy grass pollen extract (Timothy). (M) Molecular weight marker. B, C Circular dichroism analysis. B, Far-UV circular dichroism spectra of rPhl p 6, expressed as mean residue ellipticity ([Θ]) (y-axis), were recorded in the wavelength range displayed on the x-axis at 20° C. (continuous line), 85° C. (dotted line) and at 20° C. after cooling from 85° C. (dashed line). C, Thermal denaturation and cooling of purified rPhl p 6 monitored at 220 nm (x-axis: temperature in ° C.; y-axis: apparent fraction of the folded protein).
Figure 2B:
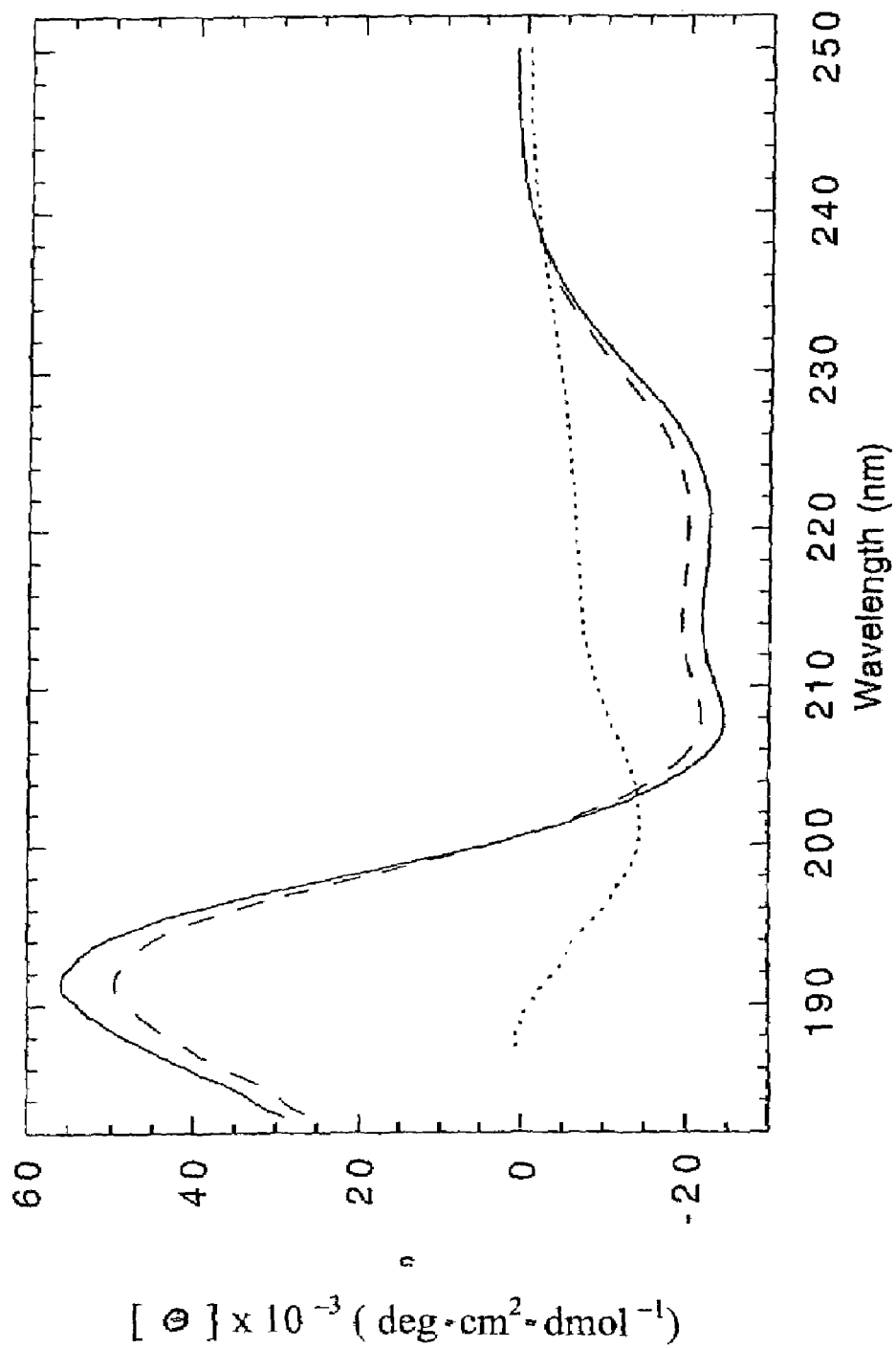
Figure 2C:
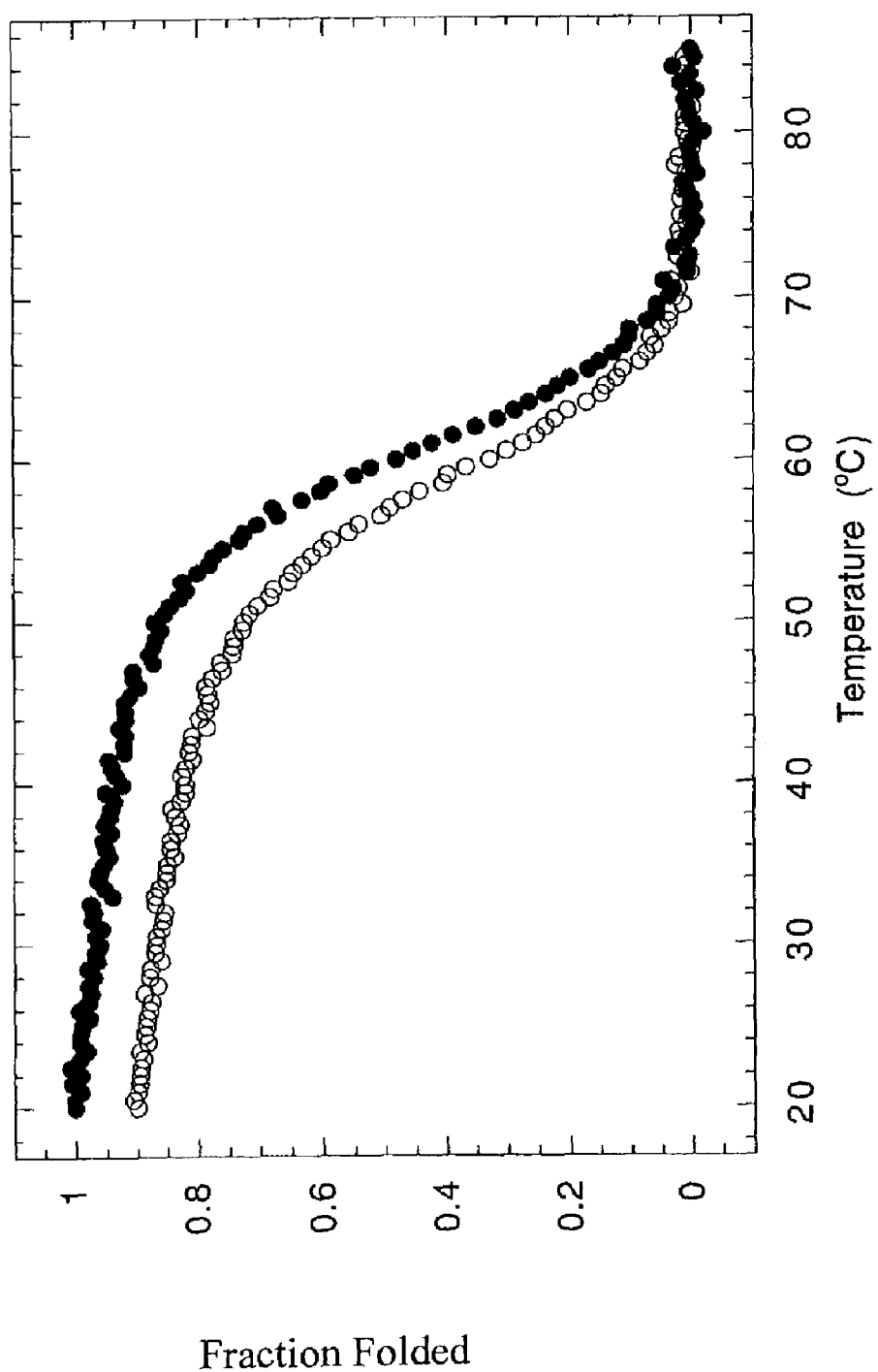
Figure 3A:
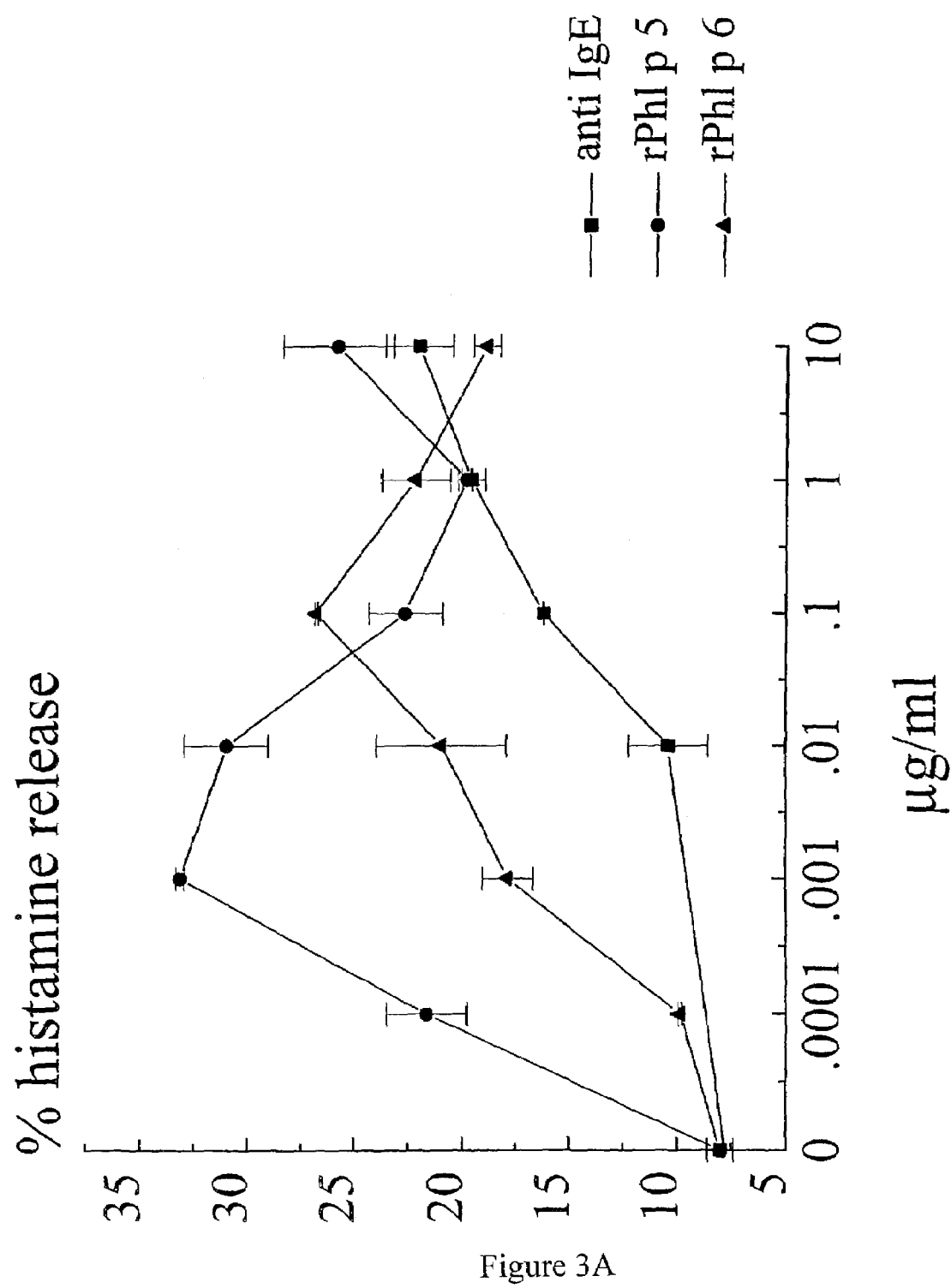
FIG. 3. A, rPhl p 6 induces basophil histamine release. Granulocytes from a grass pollen allergic patient were incubated with various concentrations (x-axis) of purified, recombinant Phl p 6 (triangles), Phl p 5 (points) or a monoclonal anti-IgE antibody (squares). The percentage of histamine released into the supernatant is displayed on the y-axis. Results represent the means (+/−SD) of triplicate determinations. B, Induction of immediate type skin reactions with rPhl p 6 in sensitized allergic patients. Two grass pollen allergic patients (a) LW, (b) HP and a non-allergic individual (c) SV were pricked on their forearms with increasing concentrations of rPhl p 6 and rPhl p 5 as well as with histamine (Hist) and NaCl as indicated in (d). The wheal area was surrounded with a ball point pen.
Figure 3B:
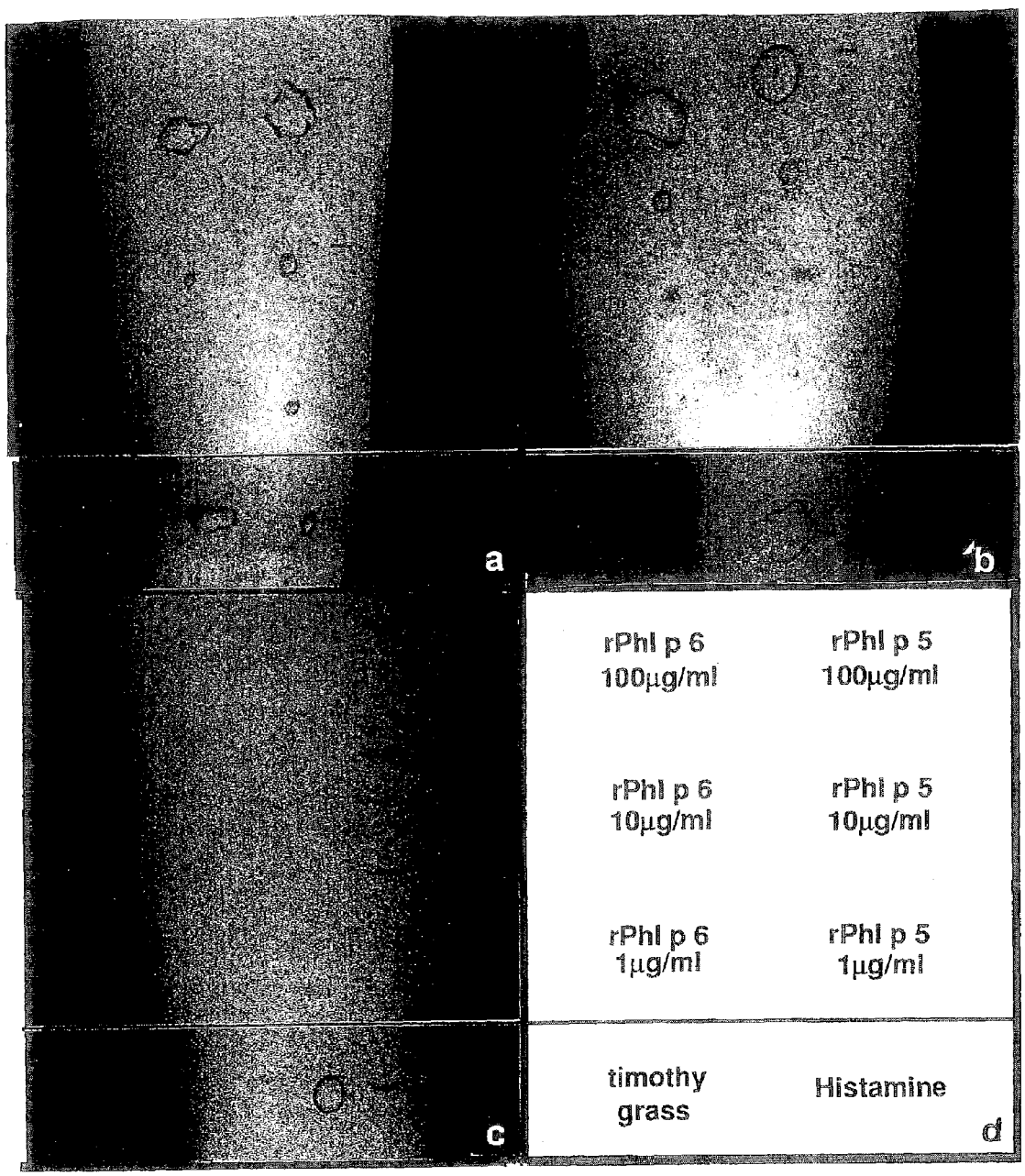
Figure 4:
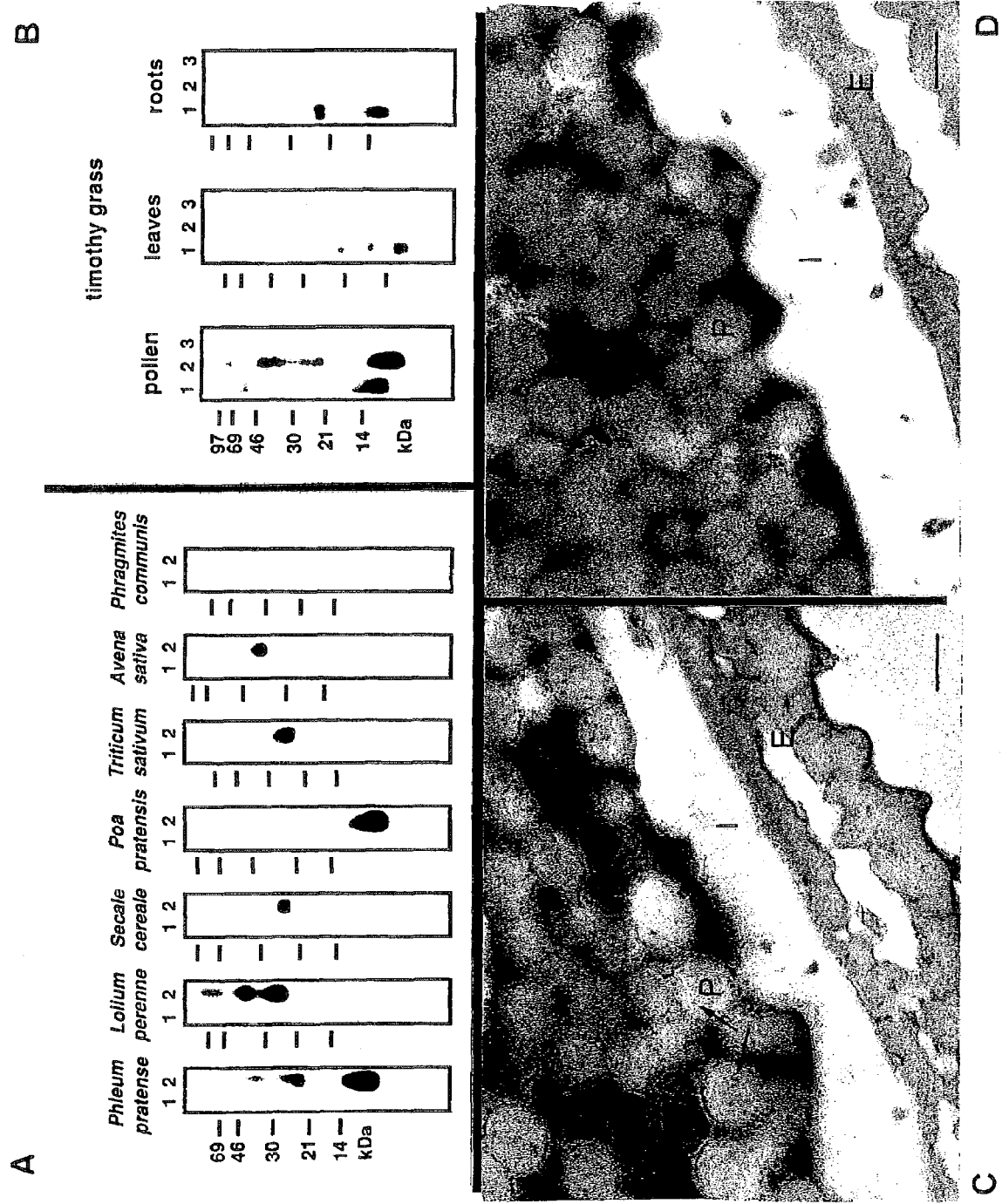
FIG. 4. Tissue-specific expression of Phl p 6. A, Nitrocellulose-blotted grass pollen extracts from various monocots were probed with rabbit preimmune Ig (lanes 1) or rabbit anti-rPhl p 6 Ig (lanes 2). B, Comparable amounts of nitrocellulose blotted protein extracts from timothy grass pollen, leaves and roots were incubated with rabbit anti-profilin Ig (lanes 1), rabbit anti-Phl p 6 Ig (lanes 2) or rabbit preimmune Ig (lanes 3). C, D, Ultrastructural localization of Phl p 6. Ultrathin sections of timothy grass pollen were stained with rabbit anti-Phl p 6 Ig (C) and with rabbit preimmune Ig (D). Bound rabbit antibodies were detected with a gold-conjugated goat anti-rabbit Ig antiserum (gold particles =black dots). Arrows indicate Phl p 6 immunoreactivity on the P-particles. Abbreviations: E: exine; I: intine; P: P-particle. The bars represent 0.250 μm.
Figure 5A:
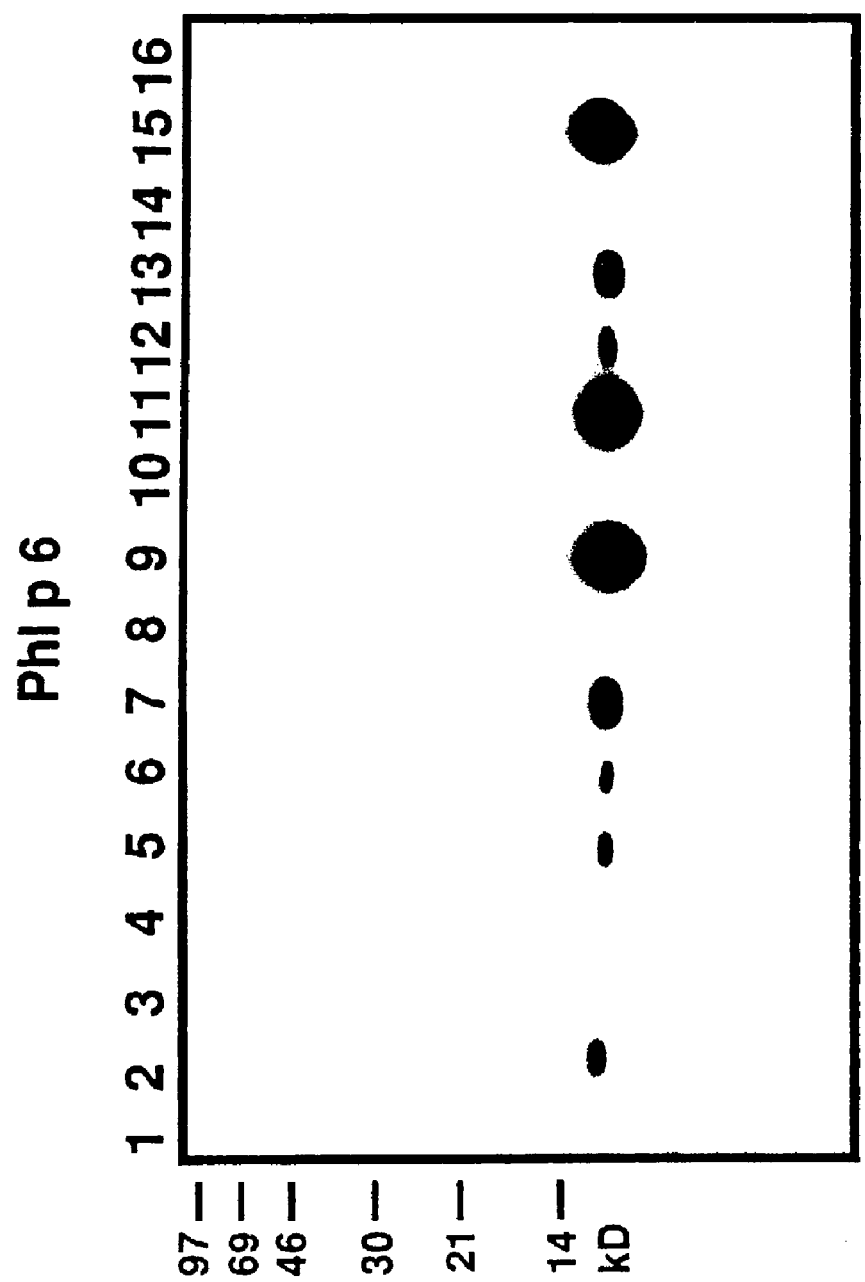
FIG. 5. Reduced IgE binding capacity of Phl p 6 deletion variants Equal amounts of recombinant Phl p 6 (A), Phl p 6 aa 1-57 (B) and Phl p 6 aa 31-110 (C) were tested for IgE-reactivity with sera from timothy grass pollen allergic patients (lane 1-13) and serum from a non-allergic control individual (lane 14). Lane 15 and lane 16 show the reactivity with a rabbit anti-Phl p 6 antiserum and a rabbit preimmunserum. Bound IgE antibodies were detected with $^{125}$I-labeled anti-human IgE antibodies, bound rabbit antibodies with $^{125}$I-labeled donkey anti-rabbit antibodies and visualized by autoradiography.
Figure 5B:
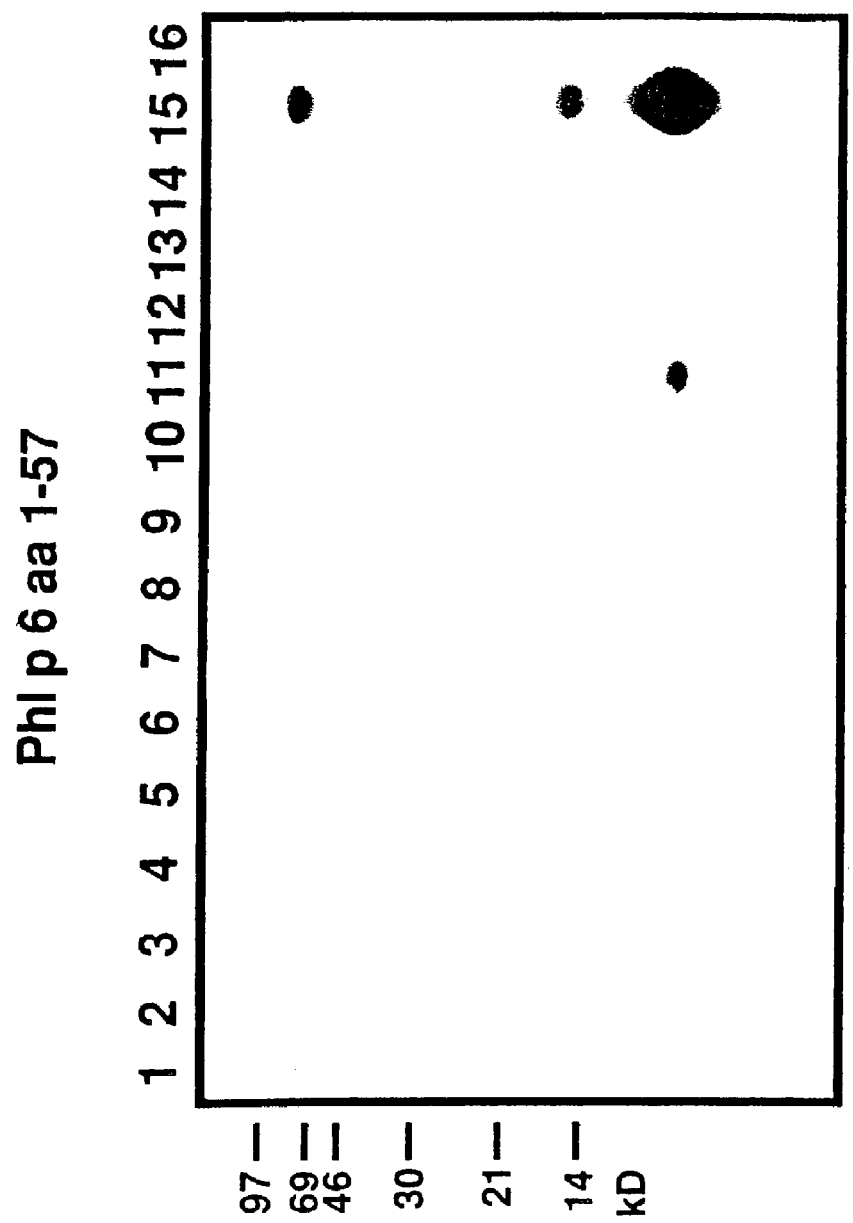
Figure 5C:
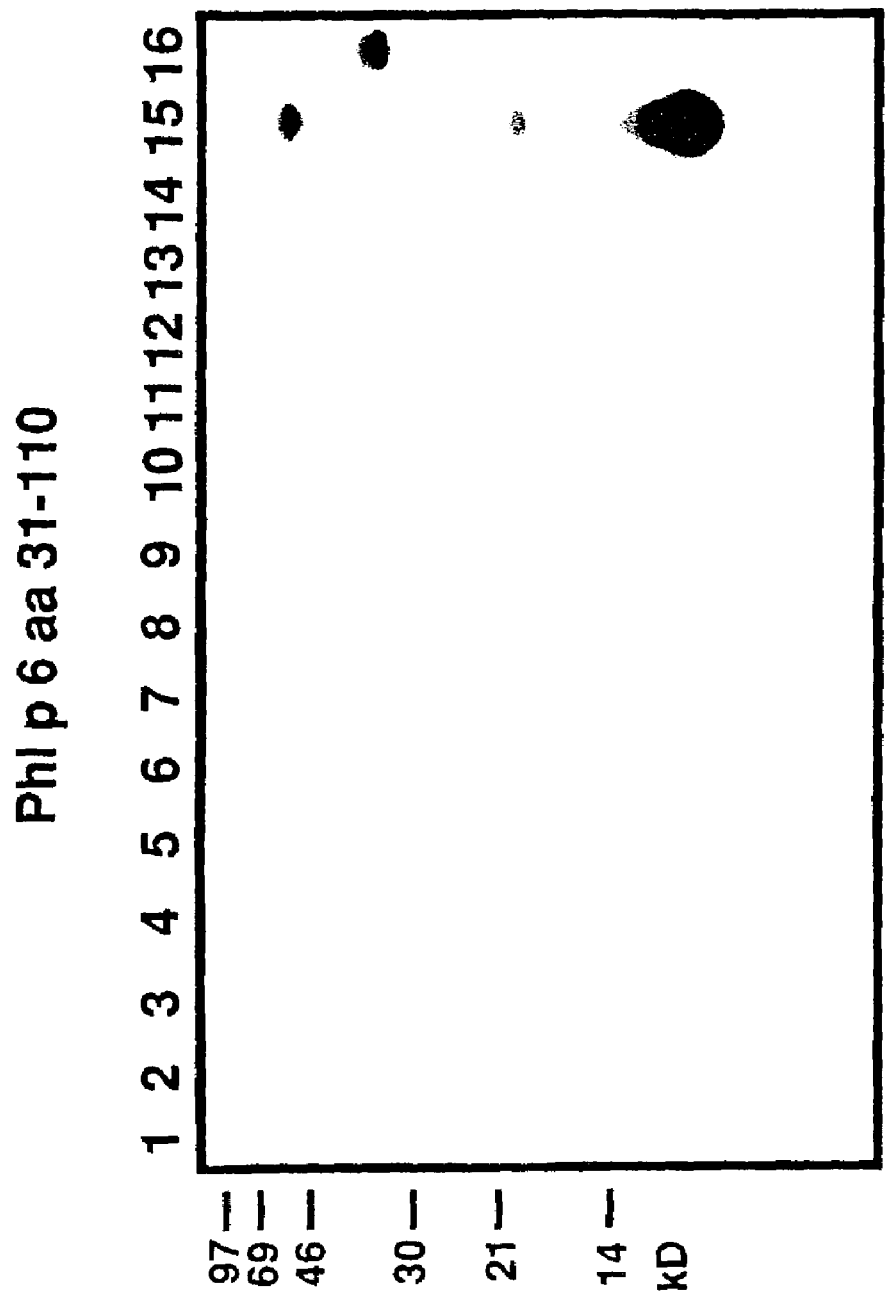
Figure 6:
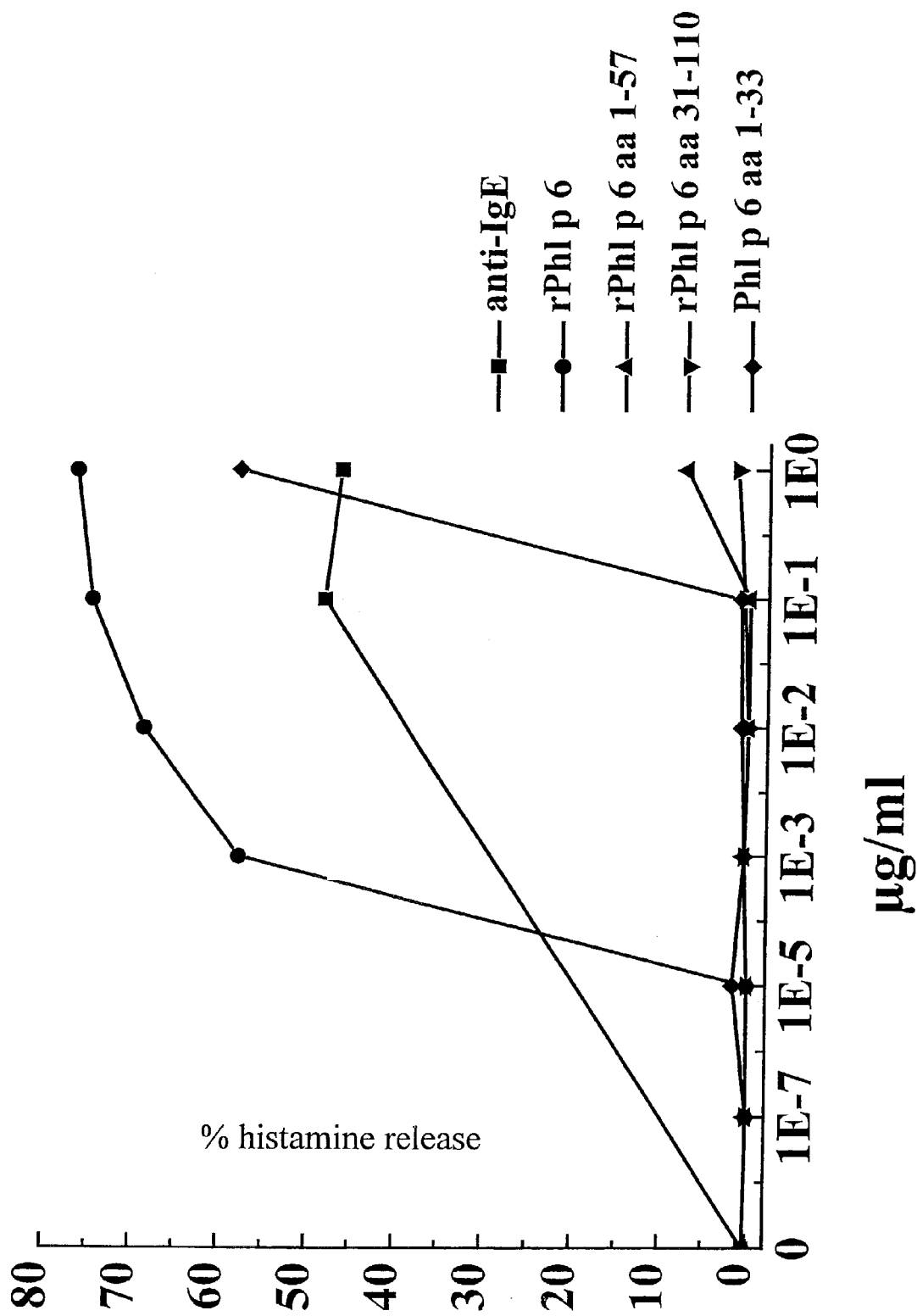
FIG. 6. Granulocytes from a patient allergic to grass pollen were incubated with various concentrations (1, $10^{-1}$, $10^{-2}$, $10^{-3}$, $10^{-5}$, and $10^{-7}$ μg/ml) of purified rPhl p 6 (points), rPhl p 6 aa 1-57 (up triangles), rPhl p 6 aa 31-110 (down triangles), rPhl p 6 aa 1-33 (rhombus) or an anti-IgE mAb (squares). Histamine released into the supernatant was measured by RIA and is displayed on the y-axis. Results represent the means of triplicate determinations.

1. Kay, A. B. 1997. *Allergy and Allergic Diseases*. Blackwell Science, Oxford, UK.
2. Segal, D. M., J. D. Taurog, and H. Metzger. 1977. Dimeric immunoglobulin E serves as a unit signal for mast cell degranulation. *Proc. Natl. Acad. Sci. USA* 41:457.
3. Freidhoff, L. R., E. Ehrlich-Kautzky, J. H. Grant, D. A. Meyers, and D. G. Marsh. 1986. A study of the human immune response to *Lolium perenne* (rye) pollen and its components, Lol p I and Lol p II (rye I and rye II). *J. Allergy Clin. Immunol.* 78:1190.
4. Niederberger, V., S. Laffer, R. Fröschl, D. Kraft, H. Rumpold, S. Kapiotis, R. Valenta, and S. Spitzauer. 1998. IgE antibodies to recombinant pollen allergens (Phl p 1, Phl p 2, Phl p 5, and Bet v 2) account for a high percentage of grass pollen-specific IgE. *J. Allergy Clin. Immunol.* 101:258.
5. Valenta, R., and D. Kraft. 1995. Recombinant allergens for diagnosis and therapy of allergic diseases. *Curr. Opin. Immunol.* 7:751.
6. Valenta, R., M. Duchêne, K. Pettenburger, C. Sillaber, P. Valent, P. Bettelheim, M. Breitenbach, H. Rumpold, D. Kraft, and O. Scheiner. 1991. Identification of profilin as a novel pollen allergen; IgE autoreactivity in sensitized individuals. *Science* 253:557.
7. Seiberler, S., O. Scheiner, D. Kraft, D. Lonsdale, and R. Valenta. 1994. Characterization of a birch pollen allergen, Bet v 3, representing a novel class of $Ca^{2+}$ binding proteins: specific expression in mature pollen and dependence of patients IgE binding on protein-bound $Ca^{2+}$. *EMBO J.* 13:3481.
8. Shcherban, T. Y., J. Shi, D. M. Durachko, M. J. Guiltinan, S. J. McQueen-Mason, M. Shieh, and D. J. Cosgrove. 1995. *Proc. Natl. Acad. Sci. USA* 92:9245.

9. Bufe, A., G. Schramm, M. B. Keown, M. Schlaak, and W. M. Becker. 1995. Major allergen Phl p 5b in timothy grass is a novel pollen RNase. *FEBS Lett.* 363:6.

10. Knox, R. B., C. Suphioglu, P. Taylor, R. Desai, H. C. Watson, J. L. Peng, and L. A. Bursill. 1997. Major grass pollen allergen Lol p 1 binds to diesel exhaust particles: implications for asthma and air pollution. *Clin. Exp. Allergy* 27:246

11. Suphioglu, C., M. B. Singh, P. Taylor, R. Bellomo, P. Holmes, R. Puy, and R. B. Knox. 1992. Mechanism of grass pollen-induced asthma. *Lancet* 339:569.

12. Vallier, P., C. Dechamp, R. Valenta, O. Vial, and P. Deviller. 1992. Purification and characterization of an allergen from celery immunochemically related to an allergen present in several other plant species. Identification as a profilin. *Clin. Exp. Allergy* 22:774.

13. Vrtala, S., M. Susani, W. R. Sperr, P. Valent, S. Laffer, C. Dolecek, D. Kraft, and R. Valenta. 1996. Immunologic characterization of purified recombinant timothy grass pollen (*Phelum pratense*) allergens (Phl p 1, Phl p 2, Phl p 5). *J. Allergy Clin. Immunol.* 97:781.

14. Vrtala, S., W. R. Sperr, I. Reimitzer, R. van Ree, S. Laffer, W.-D. Müller, P. Valent, K. Lechner, H. Rumpold, D. Kraft, O. Scheiner, and R. Valenta. 1993. cDNA cloning of a major allergen from timothy grass (*Phelum pratense*) pollen: characterization of the recombinant Phl p V allergen. *J. Immunol.* 151:4773.

15. Peterson, A., A. Bufe, G. Schramm, M. Schlaak, and W. M. Becker. 1995. Characterization of the allergen group VI in timothy grass pollen (Phl p 6). II. cDNA cloning of Phl p 6 and structural comparison to grass group V. *Int. Arch. Allergy Immunol.* 108:55.

16. Sambrook, J., E. F. Fritsch, and T. Maniatis. 1989. *Molecular cloning: A Laboratory Manual.* Cold Spring Harbor Laboratory Press, Cold Spring Harbor, N.Y.

17. Sanger, F., S. Nicklen, and A. R. Coulson. 1977. DNA sequencing with chain-terminating inhibitors. *Proc. Natl. Acad. Sci. USA* 74:5463.

18. Devereux, J., P. Haeberli, and O. Smithies. 1984. A comprehensive set of analysis programs for the VAX. *Nucl. Acids Res.* 12:387.

19. Thompson, J. D., D. G. Higgins, and T. J. Gibson. 1994. CLUSTAL W: improving the sensitivity of progressive multiple sequence alignment through sequence weighting, position-specific gap penalties and weight matrix choice. *Nucl. Acids Res.* 22:4673.

20. Rost, B., and C. Sander. 1993. Prediction of protein secondary structure at better than 70% accuracy. *J. Mol. Biol.* 232:584.

21. Ball, T., S. Vrtala, W. R. Sperr, P. Valent, M. Susani, D. Kraft, and R. Valenta. 1994. Isolation of an immunodominant IgE-hapten from an epitope expression cDNA library; dissection of the allergic effector reaction. *J. Biol. Chem.* 269:28323.

22. Valent, P., J. Besemer, M. Muhm, O. Maijdic, K. Lechner, and P. Bettelheim. 1989. Interleukin 3 activates human blood basophils via high-affinity binding sites. *Proc. Natl. Acad. Sci. USA* 86:5542.

23. Vrtala, S., K. Hirtenlehner, L. Vangelista, A. Pastore, H.-G. Eichler, W. R. Sperr, P. Valent, C. Ebner, D. Kraft, and R. Valenta. 1997. Conversion of the major birch pollen allergen, Bet v 1, into two nonanaphylactic T cell epitope-containing fragments; candidates for a novel form of specific immunotherapy. *J Clin. Invest.* 99:1673.

24. Laemmli, U. K. 1970. Cleavage of structural proteins during the assembly of the head of bacteriophage T4. *Nature* 227.680.

25. Fling, S. P., and D. S. Gregerson. 1986. Peptide and protein molecular weight determination by electrophoresis using a high molarity tris buffer system without urea. *Anal. Biochem.* 155:83.

26. Towbin, H., T. Staehelin, and J. Gordon. 1979. Electrophoretic transfers of proteins from polyacrylamide gels to nitrocellulose sheets: procedure and some applications. *Proc. Natl. Acad. Sci. USA* 76:4350.

27. Grote, M., C. Dolecek, R. vanRee, and R. Valenta. 1994. Immunogold electron microscopic localization of timothy grass (*Phelum pratense*) pollen major allergens Phl p 1 and Phl p 5 after anhydrous fixation in acrolein vapor. *J. Histochem. Cytochem.* 42.427.

28. Lowenstein, H. 1978. Isolation and partial characterization of three allergens of timothy pollen. *Allergy* 33:30.

29. Matthiesen, F., L. Friberg, M. Olsen, and H. Lowenstein. 1993. Purification and characterization of the *Phelum pratense* (timothy) pollen allergen Phl p 6. In: Molecular Biology and Immunology of Allergens. D. Kraft and A. Sehon eds. CRC Press, Boca Raton, pp. 189-191.

30. Dolecek, C., S. Vrtala, S. Laffer, P. Steinberger, D. Kraft, O. Scheiner, and R. Valenta. 1993. Molecular characterization of Phl p II, a major timothy grass (*Phelum pratense*) pollen allergen. *FEBS Lett.* 335:299.

31. Gajhede, M., P. Osmark, F. M. Poulsen, H. Ipsen, J. N. Larsen, R. J. van Neerven, C. Schou, H. Lowenstein, and M. D. Spangfort. 1996. X-ray and NMR structure of Bet v 1, the origin of birch pollen allergy. *Nature Struct. Biol.* 3:1040.

32. Fedorov, A. A., T. Ball, R. Valenta, and S. C. Almo. 1997. Crystal structure and IgE epitope mapping of birch pollen profilin: The molecular basis for allergen cross-reactivity. *Structure* 5:33.

33. Laffer, S., L. Vangelista, P. Steinberger, D. Kraft, A. Pastore, and R. Valenta. 1996. Molecular characterization of Bip 1, a monoclonal antibody that modulates IgE binding to birch pollen allergen, Bet v 1. *J. Immunol.* 157.4943.

34. Valenta, R., and D. Kraft. 1996. Type I allergic reactions to plant-derived food: A consequence of primary sensitization to pollen allergens. *J. Allergy Clin. Immunol.* 97:893.

35. Heslop-Harrison, J., and Y. Heslop-Harrison. 1982. The growth of the grass pollen tube: 1. Characteristics of the polysaccharide particles ("P-particles") associated with apical growth. *Protoplasma* 112:71.

36. Heslop-Harrison, J., Y. Heslop-Harrison, and J. S. Heslop-Harrison. 1997. Motility in ungerminated grass pollen: association of myosin with Polysaccharide'-containing wall-precursor bodies (P-particles). *Sex. Plant Reprod.* 10:65.

37. Vrtala, S., Fischer, S., Grote, M., Vangelista, L., Pastore, A., Sperr, W., Valent, P., Reichelt, R., Kraft, D., Valenta, R. 1999. Molecular, immunological, and structural characterization of Phl p 6, a major allergen and P-particle-associated protein from Timothy grass (*Phelum pratense*) pollen. *J. Immunol.* 163:5489.

TABLE I

Immediate type skin reactivity to rPhl p 6

| Individual | Phl p 6 (10 μg/ml) | Phl p 6 (100 μg/ml) | Phl p 5 (10 μg/ml) | Phl p 5 (100 μg/ml) | Timothy grass | Histamine | NaCl |
|---|---|---|---|---|---|---|---|
| Patients allergic to grasspollen | | | | | | | |
| HP | 5 | 16.5 | 5.5 | 13 | 16 | 5.5 | 0 |
| SF | 0 | 13 | 2 | 11 | 8 | 7 | 0 |
| CS | 0 | 12 | 5 | 8.5 | 12 | 9 | 0 |
| LW | 2.5 | 10.5 | 5 | 13 | 9 | 5.5 | 0 |
| Non-allergic individuals | | | | | | | |
| SV | 0 | 0 | 0 | 0 | 0 | 6 | 0 |
| SS | 0 | 0 | 0 | 0 | 0 | 7.5 | 0 |

TABLE II

IgG1-reactivity of mouse anti-rPhl p 6 or anti-rPhl p 6 aa 31-110 antisera to rPhl p 6

| | Preimmuneserum | I. Immuneserum | II. Immuneserum |
|---|---|---|---|
| Mouse anti-rPhl p 6 | | | |
| 1 | 0.060 | 0.445 | >2.5 |
| 2 | 0.061 | 1.528 | >2.5 |
| 3 | 0.065 | 0.253 | >2.5 |
| 4 | 0.061 | 0.508 | >2.5 |
| 5 | 0.062 | 0.864 | >2.5 |
| Mouse anti-rPhl p 6 aa 31-110 | | | |
| 1 | 0.063 | 1.218 | >2.5 |
| 2 | 0.056 | >2.5 | >2.5 |
| 3 | 0.057 | 0.347 | >2.5 |
| 4 | 0.054 | >2.5 | >2.5 |
| 5 | 0.056 | 0.406 | >2.5 |

The invention claimed is:

1. A hypoallergenic immunogenic composition, comprising (i) a Phl p 6 polypeptide molecule having a N-terminal truncation which makes the molecule exhibit reduced IgE binding capacity as compared with Phl p 6 and consisting of the amino acid sequence of SEQ ID NO: 18, SEQ ID NO: 19, or SEQ ID NO: 20; and (ii) a Phl p 6 polypeptide molecule having a C-terminal truncation which makes the molecule exhibit reduced IgE binding capacity as compared with Phl p 6 and consisting of the amino acid sequence of SEQ ID NO: 22, wherein the molecules of (i) and (ii) together span the complete sequence of the 110 amino acids of Phl p 6 consisting of the amino acids at positions 29-138 SEQ ID NO: 15.

2. The composition of claim 1, wherein the molecule having a N-terminal truncation is a polypeptide consisting of the amino acid sequence of SEQ ID NO: 20.

3. A hypoallergenic immunogenic composition comprising a hypoallergenic polypeptide consisting of the amino acid sequence of SEQ ID NO: 20 and a pharmaceutically acceptable carrier.

4. A hypoallergenic immunogenic composition comprising a hypoallergenic polypeptide consisting of the amino acid sequence of SEQ ID NO: 22 and a pharmaceutically acceptable carrier.

5. A method of diagnostic monitoring of Phl p 6 hyposensitization therapy which comprises exposing a first sample derived from an Ig-containing biological fluid to the hypoallergenic immunogenic composition of claim 1, and detecting antibody binding to the immunogen, and exposing a second sample derived from an Ig-containing biological fluid to the hypoallergenic immunogenic composition and detecting antibody binding to the immunogen, wherein the first sample and the second sample are obtained prior to and subsequent to, respectively, a Phl p 6 hyposensitization therapy.

6. The method of claim 5, wherein said samples derived from Ig-containing biological fluid are patient blood-derived samples.

7. An assay method for detecting IgA, IgD, IgG, IgM or mixtures thereof that specifically bind to the hypoallergenic immunogenic composition of claim 1 which comprises,
combining a sample, which may contain said antibodies with the hypoallergenic immunogenic composition of claim 1; and
detecting complexes formed between said antibodies and said hypoallergenic immunogenic composition.

8. A method of diagnostic monitoring of Phl p 6 hyposensitization therapy which comprises exposing a first sample derived from an Ig-containing biological fluid to the hypoallergenic immunogenic composition of claim 3, and detecting antibody binding to the immunogen, and exposing a second sample derived from an Ig-containing biological fluid to the hypoallergenic immunogenic composition and detecting antibody binding to the immunogen, wherein the first sample and the second sample are obtained prior to and subsequent to, respectively, a Phl p 6 hyposensitization therapy.

9. The method of claim 8, wherein said samples derived from Ig-containing biological fluid are patient blood-derived samples.

10. An assay method for detecting IgA, IgD, IgG, IgM or mixtures thereof that specifically bind to the hypoallergenic immunogenic composition of claim 3 which comprises,
combining a sample, which may contain said antibodies with the hypoallergenic immunogenic composition of claim 3; and
detecting complexes formed between said antibodies and said hypoallergenic immunogenic compositions.

11. A method of diagnostic monitoring of Phl p 6 hyposensitization therapy which comprises exposing a first sample derived from an Ig-containing biological fluid to the hypoallergenic immunogenic composition of claim 4, and detecting antibody binding to the immunogen, and exposing a second sample derived from an Ig-containing biological fluid to the hypoallergenic immunogenic composition and detecting antibody binding to the immunogen, wherein the first sample and the second sample are obtained prior to and subsequent to, respectively, a Phl p 6 hyposensitization therapy.

12. The method of claim 11, wherein said samples derived from Ig-containing biological fluid are patient blood-derived samples.

13. An assay method for detecting IgA, IgD, IgG, IgM or mixtures thereof that specifically bind to the hypoallergenic immunogenic composition of claim 4 which comprises,
combining a sample, which may contain said antibodies with the hypoallergenic immunogenic composition of claim 4; and
detecting complexes formed between said antibodies and said hypoallergenic immunogenic composition.

* * * * *

UNITED STATES PATENT AND TRADEMARK OFFICE
CERTIFICATE OF CORRECTION

PATENT NO. : 7,482,010 B2  Page 1 of 1
APPLICATION NO. : 10/305238
DATED : January 27, 2009
INVENTOR(S) : Rudolf Valenta et al.

It is certified that error appears in the above-identified patent and that said Letters Patent is hereby corrected as shown below:

Title Page

In field (75) Inventors, change "Stummfoll" to -- Stumvoll --.

In field (75) Inventors, change "Padua" to -- Padova --.

Signed and Sealed this

Twenty-fourth Day of March, 2009

JOHN DOLL
*Acting Director of the United States Patent and Trademark Office*